(12) United States Patent
Chellappa et al.

(10) Patent No.: US 7,922,781 B2
(45) Date of Patent: Apr. 12, 2011

(54) HYDROGEN GENERATION APPARATUS AND METHOD FOR USING SAME

(76) Inventors: Anand S. Chellappa, Albuquerque, NM (US); Michael Roy Powell, Kennewick, WA (US); Charles J. Call, Albuquerque, NM (US)

( * ) Notice: Subject to any disclaimer, the term of this patent is extended or adjusted under 35 U.S.C. 154(b) by 411 days.

(21) Appl. No.: 11/109,220

(22) Filed: Apr. 18, 2005

(65) Prior Publication Data
US 2005/0281735 A1 Dec. 22, 2005

Related U.S. Application Data

(63) Continuation-in-part of application No. 10/476,015, filed as application No. PCT/US02/12822 on Apr. 23, 2002, now Pat. No. 7,811,529, application No. 11/109,220, which is a continuation-in-part of application No. 10/469,464, filed as application No. PCT/US02/06767 on Mar. 4, 2002, now Pat. No. 7,875,089.

(60) Provisional application No. 60/286,114, filed on Apr. 23, 2001, provisional application No. 60/272,806, filed on Mar. 2, 2001.

(51) Int. Cl.
| | |
|---|---|
| C01B 3/36 | (2006.01) |
| C01B 3/24 | (2006.01) |
| C01B 3/02 | (2006.01) |
| C10J 3/46 | (2006.01) |
| B01J 7/00 | (2006.01) |

(52) U.S. Cl. ........ 48/197 R; 48/198.3; 48/61; 423/648.1
(58) Field of Classification Search .................. 48/198.3, 48/61, 197 R; 423/648.1
See application file for complete search history.

(56) References Cited

U.S. PATENT DOCUMENTS

| | | | |
|---|---|---|---|
| 3,480,419 A | 11/1969 | Louis et al. | |
| 3,505,027 A | 4/1970 | Breitbach et al. | |
| 3,682,142 A | 8/1972 | Newkirk | |
| 3,907,511 A | 9/1975 | Forbes et al. | |
| 4,088,450 A | 5/1978 | Kosaka et al. | |
| 4,098,587 A | 7/1978 | Krar et al. | |
| 4,098,588 A | 7/1978 | Buswell et al. | |
| 4,098,589 A | 7/1978 | Buswell et al. | |
| 4,106,439 A | 8/1978 | Kanao | |
| 4,113,838 A | 9/1978 | Koike et al. | |
| 4,155,712 A | 5/1979 | Taschek | |

(Continued)

FOREIGN PATENT DOCUMENTS
DE 39 26 466 C2 2/1991

(Continued)

*Primary Examiner* — Alexa D Neckel
*Assistant Examiner* — Matthew J Merkling
(74) *Attorney, Agent, or Firm* — Mark H. Krietzman; Baker & Hostetler, LLP

(57) ABSTRACT

A compact hydrogen generator for use with fuel cells and other applications includes a hydrogen membrane reactor having a combustion chamber and a reaction chamber. The two chambers are have a fluid connection and a heat exchange relationship with one another. The hydrogen generation apparatus also includes a fuel supply, a fuel supply line for transporting fuel from the fuel supply to the reaction chamber, an oxygen supply, an oxygen supply line for transporting oxygen from the oxygen supply to the combustion chamber, as well as a tail gas supply line for transporting tail gas supply line for transporting tail gases from the reaction chamber, a combustion by-product line for transporting combustion by-products for the combustion chamber, and a reaction product line for transporting hydrogen from the reaction chamber.

19 Claims, 12 Drawing Sheets

U.S. PATENT DOCUMENTS

| | | |
|---|---|---|
| 4,157,270 A | 6/1979 | Martingnoni et al. |
| 4,211,537 A | 7/1980 | Teitel |
| 4,248,941 A | 2/1981 | Louis et al. |
| 4,293,315 A | 10/1981 | Sederquist |
| 4,438,082 A | 3/1984 | Dettling |
| 4,454,207 A | 6/1984 | Frioli et al. |
| 4,624,841 A | 11/1986 | Hidaki |
| 4,650,727 A | 3/1987 | Vanderborgh et al. |
| 4,670,359 A | 6/1987 | Beshty et al. |
| 4,692,306 A | 9/1987 | Minet et al. |
| 4,737,161 A | 4/1988 | Szydiowski et al. |
| 4,746,329 A | 5/1988 | Christner et al. |
| 4,761,164 A | 8/1988 | Pez et al. |
| 4,781,241 A * | 11/1988 | Misage et al. ............... 165/140 |
| 4,861,347 A | 8/1989 | Szydiowski et al. |
| 4,933,242 A | 6/1990 | Koga et al. |
| 5,015,444 A | 5/1991 | Koga et al. |
| 5,084,363 A | 1/1992 | Reiser |
| 5,215,729 A | 6/1993 | Buxbaum |
| 5,221,524 A | 6/1993 | Eguchi |
| 5,222,551 A | 6/1993 | Hasegawa et al. |
| 5,360,461 A | 11/1994 | Meinzer |
| 5,389,230 A | 2/1995 | Veluswamy |
| 5,432,023 A | 7/1995 | Yamada et al. |
| 5,601,937 A | 2/1997 | Isenberg |
| 5,609,834 A | 3/1997 | Hamada et al. |
| 5,612,012 A | 3/1997 | Soma |
| 5,618,322 A | 4/1997 | Mizuno |
| 5,631,099 A | 5/1997 | Hockaday |
| 5,641,585 A | 6/1997 | Lessing |
| 5,648,182 A | 7/1997 | Hara et al. |
| 5,652,020 A | 7/1997 | Collins et al. |
| 5,676,911 A | 10/1997 | Baumert et al. |
| 5,686,196 A | 11/1997 | Singh et al. |
| 5,702,491 A | 12/1997 | Long et al. |
| 5,733,347 A | 3/1998 | Lesieur |
| 5,741,474 A | 4/1998 | Isomura |
| 5,746,985 A | 5/1998 | Takahashi |
| 5,759,712 A | 6/1998 | Hockaday |
| 5,776,421 A | 7/1998 | Matsumura et al. |
| 5,780,179 A | 7/1998 | Okamoto |
| 5,811,062 A | 9/1998 | Wegeng et al. |
| 5,858,314 A | 1/1999 | Hsu |
| 5,861,137 A | 1/1999 | Edlund |
| 5,888,273 A | 3/1999 | Buxbaum |
| 5,897,970 A | 4/1999 | Isomura et al. |
| 5,904,754 A | 5/1999 | Juda et al. |
| 5,938,800 A | 8/1999 | Verrill |
| 5,942,346 A | 8/1999 | Ahmed et al. |
| 5,961,932 A | 10/1999 | Ghosh et al. |
| 5,976,725 A | 11/1999 | Gamo et al. |
| 5,980,726 A | 11/1999 | Moulthrop, Jr. et al. |
| 5,997,594 A | 12/1999 | Edlund |
| 6,007,606 A | 12/1999 | Baksh et al. |
| 6,007,699 A | 12/1999 | Cole |
| 6,045,933 A | 4/2000 | Okamoto |
| 6,057,051 A | 5/2000 | Uchida et al. |
| 6,083,425 A | 7/2000 | Clawson et al. |
| 6,096,286 A | 8/2000 | Autenriieth |
| 6,103,143 A | 8/2000 | Sircar et al. |
| 6,103,411 A | 8/2000 | Matsubayashi et al. |
| 6,122,909 A * | 9/2000 | Murphy et al. ............... 60/286 |
| 6,126,723 A | 10/2000 | Drost et al. |
| 6,126,908 A | 10/2000 | Clawson et al. |
| 6,129,861 A | 10/2000 | Muesinger et al. |
| 6,152,987 A | 11/2000 | Ma et al. |
| 6,152,995 A | 11/2000 | Edlund |
| 6,159,434 A | 12/2000 | Gonjo et al. |
| 6,171,574 B1 | 1/2001 | Juda et al. |
| 6,180,846 B1 | 1/2001 | Dandekar et al. |
| 6,183,703 B1 | 2/2001 | Hsu et al. |
| 6,183,895 B1 * | 2/2001 | Kudo et al. ............... 429/20 |
| 6,190,623 B1 | 2/2001 | Sanger et al. |
| 6,190,624 B1 | 2/2001 | Romatier |
| 6,192,596 B1 | 2/2001 | Bennett et al. |
| 6,200,536 B1 | 3/2001 | Tonkovich et al. |
| 6,207,122 B1 | 3/2001 | Clawson et al. |
| 6,207,132 B1 | 3/2001 | Lin et al. |
| 6,221,117 B1 | 4/2001 | Edlund et al. |
| 6,231,831 B1 | 5/2001 | Autenrieth et al. |
| 6,232,005 B1 | 5/2001 | Pettit |
| 6,238,465 B1 | 5/2001 | Juda et al. |
| 6,242,120 B1 | 6/2001 | Herron |
| 6,244,367 B1 | 6/2001 | Ahmed et al. |
| 6,245,303 B1 | 6/2001 | Bentley et al. |
| 6,245,309 B1 | 6/2001 | Etievant et al. |
| 6,254,839 B1 | 7/2001 | Clawson et al. |
| 6,254,848 B1 | 7/2001 | Autenrieth et al. |
| 6,264,856 B1 | 7/2001 | Autenrieth et al. |
| 6,268,077 B1 | 7/2001 | Kelley et al. |
| 6,269,625 B1 * | 8/2001 | Dibble et al. ............... 60/777 |
| 6,274,093 B1 | 8/2001 | Long et al. |
| 6,280,864 B1 | 8/2001 | Towler et al. |
| 6,284,398 B1 | 9/2001 | Kiryu |
| 6,294,276 B1 | 9/2001 | Ogino |
| 6,296,814 B1 | 10/2001 | Bonk et al. |
| 6,299,744 B1 | 10/2001 | Narayanan et al. |
| 6,299,994 B1 | 10/2001 | Towler et al. |
| 6,319,306 B1 | 11/2001 | Edlund et al. |
| 6,326,097 B1 | 12/2001 | Hockaday |
| 6,329,091 B1 | 12/2001 | James |
| 6,331,281 B1 | 12/2001 | Teru et al. |
| 6,338,913 B1 | 1/2002 | Eshraghi |
| 6,348,278 B1 | 2/2002 | LaPierre et al. |
| 6,350,297 B1 | 2/2002 | Doyle et al. |
| 6,352,792 B1 | 3/2002 | Parchamazad |
| 6,368,735 B1 | 4/2002 | Lomax et al. |
| 6,372,363 B1 | 4/2002 | Krueger |
| 6,375,906 B1 | 4/2002 | Edlund et al. |
| 6,376,113 B1 | 4/2002 | Edlund et al. |
| 6,383,670 B1 | 5/2002 | Edlund et al. |
| 6,413,479 B1 * | 7/2002 | Kudo et al. ............... 422/198 |
| 6,419,728 B1 | 7/2002 | Edlund |
| 6,451,464 B1 | 9/2002 | Edlund et al. |
| 6,458,189 B1 | 10/2002 | Edlund et al. |
| 6,465,118 B1 | 10/2002 | Dickman et al. |
| 6,470,569 B1 | 10/2002 | Lippert et al. |
| 6,503,298 B1 | 1/2003 | Monzyk et al. |
| 6,627,338 B2 | 9/2003 | St-Pierre et al. |
| 6,653,005 B1 | 11/2003 | Muradov |
| 6,869,707 B2 | 3/2005 | Edlund et al. |
| 7,048,897 B1 | 5/2006 | Koripella et al. |
| 7,056,369 B2 | 6/2006 | Beisswenger et al. |
| 7,077,643 B2 | 7/2006 | Holladay et al. |
| 2001/0000380 A1 | 4/2001 | Buxbaum |
| 2001/0018140 A1 | 8/2001 | Hermann et al. |
| 2001/0021359 A1 | 9/2001 | Johnston |
| 2001/0045061 A1 | 11/2001 | Edlund et al. |
| 2001/0045364 A1 | 11/2001 | Hockaday et al. |
| 2001/1045061 | 11/2001 | Buxbaum |
| 2001/0049038 A1 | 12/2001 | Dickman et al. |
| 2001/0049907 A1 * | 12/2001 | Inoue ............... 48/76 |
| 2001/0053472 A1 | 12/2001 | Edlund |
| 2002/0000066 A1 | 1/2002 | Bentley et al. |
| 2002/0000067 A1 | 1/2002 | Numata et al. |
| 2002/0006369 A1 | 1/2002 | Buxbaum |
| 2002/0007594 A1 | 1/2002 | Muradov |
| 2002/0021992 A1 | 2/2002 | Bass et al. |
| 2002/0022167 A1 | 2/2002 | Herron |
| 2002/0025458 A1 * | 2/2002 | Faville et al. ............... 429/13 |
| 2002/0028171 A1 | 3/2002 | Goetsch et al. |
| 2002/0071976 A1 | 6/2002 | Edlund |
| 2002/0083645 A1 | 7/2002 | Edlund |
| 2002/0083829 A1 | 7/2002 | Edlund et al. |
| 2002/0086987 A1 | 7/2002 | Hair et al. |
| 2002/0114762 A1 | 8/2002 | Wong et al. |
| 2002/0114984 A1 | 8/2002 | Edlund et al. |
| 2002/0116872 A1 | 8/2002 | Edlund et al. |
| 2002/0119353 A1 | 8/2002 | Edlund et al. |
| 2002/0127445 A1 * | 9/2002 | Carpenter et al. ............... 429/19 |
| 2002/0127447 A1 | 9/2002 | Edlund et al. |
| 2002/0146604 A1 * | 10/2002 | Matoba ............... 429/20 |
| 2003/0055585 A1 | 3/2003 | Stoupis et al. |
| 2003/0068269 A1 | 4/2003 | Matzakos et al. |
| 2003/0191199 A1 | 10/2003 | O'Rear |
| 2003/0232224 A1 | 12/2003 | Kordesch et al. |
| 2004/0154223 A1 | 8/2004 | Powell et al. |

| | | | |
|---|---|---|---|
| 2004/0187386 A1* | 9/2004 | Wangerow et al. .......... 48/198.3 |
| 2004/0191137 A1 | 9/2004 | Chellappa |
| 2004/0194626 A1 | 10/2004 | Chellappa et al. |
| 2004/0219423 A1 | 11/2004 | Tunney et al. |
| 2005/0016729 A1 | 1/2005 | Savage |
| 2005/0022448 A1 | 2/2005 | Kaye |
| 2005/0039400 A1 | 2/2005 | Lau et al. |
| 2005/0042165 A1 | 2/2005 | Akiyama et al. |
| 2005/0244684 A1 | 11/2005 | Koripella |

FOREIGN PATENT DOCUMENTS

| | | |
|---|---|---|
| DE | 19902926 A1 | 3/2000 |
| EP | 0 861 802 A2 | 2/1998 |
| EP | 0 906 890 A1 | 4/1999 |
| EP | 1 061 039 C2 | 12/2000 |
| GB | 97 21 66 | 10/1964 |
| JP | 54023942 | 2/1979 |
| JP | 58-0119166 | 7/1983 |
| JP | 9501649 T | 11/1994 |
| JP | 10330992 | 12/1998 |
| JP | 2000510526 T | 4/1999 |
| JP | 11255501 A | 9/1999 |
| JP | 2000159502 A | 6/2000 |
| JP | 20000281312 A | 10/2000 |
| JP | 2002305012 A | 10/2002 |
| JP | 2004502623 T | 1/2004 |
| JP | 2004525058 T | 8/2004 |
| WO | WO 96/29751 | 9/1996 |
| WO | WO 97/17125 | 5/1997 |
| WO | WO 98/00878 | 1/1998 |
| WO | WO 99/17867 | 4/1999 |
| WO | WO 99/43610 | 9/1999 |
| WO | WO 99/64146 | 12/1999 |
| WO | WO 99/66279 | 12/1999 |
| WO | WO 0112539 | 2/2001 |
| WO | WO 0126174 | 4/2001 |
| WO | WO 0150541 | 7/2001 |
| WO | WO 0177011 | 10/2001 |
| WO | WO 02/071451 A2 | 9/2002 |
| WO | WO 02/086987 A2 | 10/2002 |
| WO | WO 03/035547 AI | 5/2003 |
| WO | WO 03/055585 | 7/2003 |
| WO | WO03055585 A1 | 7/2003 |
| WO | WO03087264 A2 | 10/2003 |
| WO | WO2005001003 A2 | 1/2005 |

* cited by examiner

_US 7,922,781 B2_

HYDROGEN GENERATION APPARATUS AND METHOD FOR USING SAME

RELATED APPLICATIONS

This application is a continuation-in-part of, and claims priority to U.S. application Ser. No. 10/476,015, entitled "HYDROGEN GENERATION APPARATUS AND METHOD FOR USING SAME", filed on Oct. 23, 2003 and having 371 date of Apr. 27, 2004, now U.S. Pat. No. 7,811,529 which is a national phase filing of PCT International Application No. PCT/US02/12822, filed Apr. 23, 2002 and which claims priority to U.S. Provisional Application No. 60/286,114, filed Apr. 23, 2001, all of which are herein incorporated by referenced in their entirety. This application is also a continuation-in-part and claims priority to U.S. application Ser. No. 10/469,464 filed Aug. 29, 2003 and having a 371 date of Mar. 22, 2004, now U.S. Pat. No. 7,875,089 which is a national phase filing of International Application No. PCT/US02/06767, filed on Mar. 4, 2002, which claims priority U.S. Provisional Patent Application No. 60/272,806, filed Mar. 2, 2001, all herein incorporated by reference in their entirety. This application is also related to U.S. application Ser. No. 11/109,227, entitled "Ammonia-Based Hydrogen Generation Apparatus" filed on Apr. 18, 2005, and to U.S. application Ser. No. 11/109,186, entitled "Compact Devices for Generating Pure Hydrogen" filed on Apr. 18, 2005, herein also incorporated by reference in their entirety

GOVERNMENT RIGHTS

This invention was made under contract with the United States Army Research Office, under Contract No. DAAD19-01-C-0015, and the United States Government may have certain rights in the invention.

BACKGROUND OF THE INVENTION

1. Field of the Invention

The present invention generally relates to the chemical arts. More particularly, the present invention relates to an apparatus and method for generating hydrogen gas by decomposing or reforming a liquid fuel.

2. General Background and State of the Art

The growing popularity of portable electronic devices has produced an increased demand for compact and correspondingly portable electrical power sources to energize these devices. Developments in robotics and other emerging technology applications are further increasing the demand for small, independent power sources.

At present, storage or rechargeable batteries are typically used to provide independent electrical power sources for portable devices. However, the amount of energy that can be stored in storage or rechargeable batteries is insufficient to meet the need of certain applications.

Hydrogen/air fuel cells (H/AFCs) have enormous potential as a replacement for batteries. Because they can operate on very energy-dense fuels, fuel cell-based power supplies offer high energy-to-weight ratios compared with even state-of-the-art batteries. Fuel cells are of particular interest to the military, where significant efforts are being made to reduce the weight of power supplies that soldiers must carry to support high-tech, field-portable equipment. There is also considerable potential for utilizing fuel cell-based power supplies for commercial applications, particularly where small size and low weight are desirable.

A common H/AFC is a polymer electrolyte membrane (PEM) fuel cell. PEM fuel cells are constructed of an anode and a cathode separated by a polymer electrolyte membrane.

Functionally, fuel cells generate electricity by reacting hydrogen with oxygen to produce water. Since oxygen can typically be obtained from the ambient atmosphere, only a source of hydrogen must be provided to operate a fuel cell. Merely providing compressed hydrogen is not always a viable option, because of the substantial volume that even a highly compressed gas occupies. Liquid hydrogen, which occupies less volume, is a cryogenic liquid, and a significant amount of energy is required to maintain the extremely low temperatures required to maintain it as a liquid. Furthermore, there are safety issues involved with the handling and storage of hydrogen in the compressed gas form or in the liquid form.

Several alternative approaches are available. These alternatives include ammonia decomposition and hydrocarbon reformation. Ammonia decomposition is relatively easy. Ammonia can be thermo-catalytically cracked at relatively low temperatures to produce a gas mixture that is 75% hydrogen by volume. Hydrocarbon fuels are somewhat more technically challenging, because hydrocarbon reformation requires relatively higher temperatures, and the simple cracking of hydrocarbons produces a solid residue which is undesirable in a fuel cell application. However, the reformation of hydrocarbon fuels offers the incentive of enabling a higher energy density fuel to be used, as compared with the use of ammonia as a fuel source, i.e., the production of a greater mass of hydrogen per unit mass of fuel. Consequently, there is a desideratum for an apparatus that has the flexibility to effectively and efficiently generate hydrogen from either ammonia or hydrocarbon fuel.

The ammonia decomposition reaction can be represented as follows:

$$2NH_3 \rightarrow N_2 + 2H_2 \qquad (1)$$

The simple hydrocarbon cracking reaction can be represented as follows:

$$C_nH_{(2n+2)} \rightarrow C_{n(solid)} + (n+1)H_2 \qquad (2)$$

The formation of solid residues can be avoided through the use of oxidative cracking processes or by employing steam reforming. Oxidative cracking be represented as follows:

$$C_nH_{(2n+2)}O_2 \rightarrow nCO_2 + (n+1)H_2 \qquad (3)$$

Steam reforming can be represented as follows:

$$C_nH_{(2n+2)}2_nH_2O \rightarrow nCO_2 + (3_n+1)H_2 \qquad (4)$$

It is a drawback of ammonia decomposition that traces of un-reacted ammonia (typically <2000 ppm) remain in the product gas stream. One of the challenges of utilizing ammonia to produce hydrogen for a fuel cell is that H/AFCs do not tolerate ammonia in the hydrogen feed gas, so the trace amounts of ammonia in the hydrogen produced by an ammonia cracker must be removed before the remaining $H_2/N_2$ mixture is supplied to a fuel cell.

It is a drawback of hydrocarbon reformulation that the actual product is a mixed gas stream that contains substantial amounts of carbon monoxide (CO). Furthermore, the product is a gas stream that also contains partially oxidized hydrocarbons. Both carbon dioxide and partially oxidized hydrocarbons can poison the anode electro-catalysts used in PEM fuel cells. Thus, utilizing either ammonia decomposition, oxidative cracking or steam reforming requires additional steps to purify the hydrogen, or decompose the impurities. Such additional processes add size, cost, and complexity to a hydrogen generation system, making achieving a compact, low cost, and portable system more difficult. Therefore, it is also a desideratum to provide a hydrogen generation system that can be used to provide hydrogen to a fuel cell, which requires minimal or no additional processing to purify the hydrogen that is produced before such hydrogen can be used in a fuel cell.

To compete with battery-based power supplies, such an H/AFC apparatus needs to be compact and reliable. It is a further desideratum to develop a portable hydrogen supply with a volume less than 1 liter and a mass less than 1 kg that can produces up to 50 watts of electrical power, with a total energy output of 1 kWh. Commercially available metal hydride storage cylinders are available in 920 gm cylinders that contain the equivalent of 100 W-h of hydrogen.

Thus, a total energy output of 1 kWh represents an order of magnitude increase in energy density over commercially available apparatuses.

SUMMARY OF THE INVENTION

Now in accordance with this invention there has been found a compact hydrogen generation apparatus for use with fuel cells and other applications. The hydrogen generator includes a hydrogen membrane reactor having a combustion chamber and a reaction chamber. The two chambers are in fluid connection and a heat exchange relationship with one another. The hydrogen membrane reactor also includes a fuel inlet into the reaction zone, an oxygen inlet into the combustion chamber, a tail gas outlet out of the reaction zone, a hydrogen outlet out of the hydrogen exhaust zone, and a by-product outlet out of the combustion chamber.

The hydrogen generation apparatus also includes a fuel supply, a fuel supply line for transporting fuel from the fuel supply to the reaction chamber, an oxygen supply, an oxygen supply line for transporting oxygen from the oxygen supply to the combustion chamber, as well as a tail gas supply line for transporting tail gases from the reaction chamber, a combustion byproduct line for transporting combustion by-products from the combustion chamber, and a reaction product line for transporting hydrogen from the reaction chamber.

In some embodiments, the hydrogen membrane reactor is formed of a top plate, a bottom plate, and a separation plate having first and second opposing surfaces. The top plate and the first surface of the separation plate together define the reaction chamber, while the bottom plate and the second surface of the separation plate together define the combustion chamber. A hydrogen separation membrane having first and second opposing surfaces is disposed between the top plate and the separation plate, so that the top plate and the first surface of the hydrogen separation membrane together define a hydrogen exhaust zone, while the separation plate and the second surface of the hydrogen separation membrane together define a reaction zone. In these embodiments, the fuel supply line transports fuel to the reaction zone, the tail gas supply line transports tail gas from the reaction zone, and the reaction product line transports hydrogen from the hydrogen exhaust zone.

In some embodiments, the combustion chamber has a plurality of combustion channels extending radially from the surface of the separation plate and forming a fluid path through the combustion chamber, the hydrogen exhaust zone has a plurality of hydrogen exhaust channels extending radially from the first surface of the hydrogen membrane and forming a fluid path through the hydrogen exhaust zone, and the reaction zone has a plurality of reaction channels extending radially from the second surface of the hydrogen membrane and forming a fluid path through the reaction zone. The height and width of each of the combustion channels, the hydrogen exhaust channels, and the reaction channels is preferably between 0.01 mm and 10 mm and more preferably between 0.5 mm and 5 mm.

In some embodiments, the tail gas supply line makes a direct fluid connection between the reaction zone and the combustion chamber. In other embodiments, the tail gas supply line makes an indirect fluid connection between the reaction zone and the combustion chamber via the oxygen supply line.

Some embodiments additionally include a fuel heat exchanger operably connected to the fuel supply line and one of the combustion by-product line or the reaction product line. In preferred embodiments, the fuel heat exchanger is operably connected to the reaction byproduct line. Some embodiments additionally include an oxygen heat exchanger operably connected to the oxygen supply line and one of the combustion by-product line or the reaction product supply line. In preferred embodiments, the oxygen heat exchanger is operably connected to the combustion product line.

In preferred embodiments, the fuel heat exchanger and/or the oxygen heat exchanger are counterflow-type heat exchangers. In more preferred embodiments, the fuel heat exchanger and/or the oxygen heat exchanger are stacked-plate-type heat exchangers having channels with a height and a width between about 0.01 mm and 10 mm running between the stacked plates.

Some embodiments additionally include a hydrogen reservoir in fluid connection with the reaction product supply line. A hydrogen fuel cell in fluid connection with the reaction product supply line is included in some embodiments.

In some embodiments, a combustion catalyst in included the combustion chamber. The combustion catalyst and the reaction catalyst can be packed in or coated on the internal surfaces of the combustion and/or reaction channels, respectively.

In some embodiments, the fuel supply is an ammonia supply. These embodiments can additionally include an ammonia adsorbent supply in fluid communication with the reaction product line.

In other embodiments, the fuel supply is a hydrocarbon supply. Suitable hydrocarbon fuel supplies include methanol, propane, butane, and kerosene fuel supplies.

Also in accordance with the invention there has been found a method for generating hydrogen. In a first step a hydrogen-producing fuel is flowed through the reaction zone and into the combustion chamber of the hydrogen membrane reactor. The reaction zone contains a reaction catalyst initially at a temperature less than the reaction catalyst's light-off temperature. In preferred embodiments, the light off temperature of the reaction catalyst is less than 650° C. Suitable reaction catalysts include ruthenium catalysts, nickel catalysts, iron oxide catalysts, rhodium catalysts, iridium catalysts or rhenium catalysts.

The hydrogen-producing fuel is then combusted to produce combustion by-products while raising the temperature of the reaction catalyst in the reaction zone and the combustion by-products are exhausted. Combustion of the hydrogen-producing fuel is continued for a period of time sufficient to raise the temperature of the reaction catalyst to above its light off temperature.

Additional hydrogen-producing fuel is flowed into the reaction chamber and reacted to produce hydrogen and tail gases. The hydrogen is then separated from the tail gases by selectively removing the hydrogen from the mixture including tail gases through the hydrogen membrane.

In some embodiments, the combustion chamber contains a combustion catalyst having a light-off temperature. In preferred embodiments, the combustion catalyst also has a light off temperature of less than 650° C. Suitable combustion catalysts include platinum-rhodium catalysts.

In some embodiments, the tail gas is recirculated from the reaction zone into the combustion chamber. In some embodiments, the hydrogen-producing fuel is pre-heated prior to flowing the hydrogen producing fuel into the reaction zone. And some embodiments include flowing oxygen, preferably pre-heated oxygen into the combustion chamber.

In some embodiments, the separated hydrogen is flowed into a hydrogen reservoir. In other embodiments the separated hydrogen is flowed into a hydrogen fuel cell.

In some embodiments, the hydrogen-producing fluid is ammonia, and in some of these embodiments, the separated hydrogen is flowed through an ammonia adsorbent. In other embodiments, the hydrogen-producing fluid is a hydrocarbon. Preferred hydrocarbons include methanol, propane, butane, and kerosene.

In some embodiments, the hydrogen generator comprises a hydrogen membrane reactor having a combustion chamber and a reaction chamber, at least one fuel supply; a fuel supply line; an oxygen supply; an oxygen supply line; a second fuel supply line; a tail gas supply line; a combustion by-product line; and a reaction product line. In this embodiment the combustion chamber is in a fluid connection with and a heat exchange relationship with the reaction chamber that includes a reaction zone and a hydrogen exhaust zone.

In the hydrogen membrane reactor, the combustion chamber comprises a plurality of combustion channels creating a fluid path through the combustion chamber, the reaction zone comprises a plurality of reaction channels extending radially from the second surface of the separation plate, creating a fluid path through the reaction zone and the hydrogen exhaust zone comprises a plurality of hydrogen exhaust channels creating a fluid path through the hydrogen exhaust zone.

In the hydrogen generator, the oxygen supply line is for transporting oxygen from the oxygen supply to the combustion chamber; the second fuel supply line is for transporting fuel from the fuel supply to the combustion chamber; the tail gas supply line is for transporting tail gases from the reaction chamber; the combustion by-product line is for transporting combustion by-products from the combustion chamber; and the reaction product line is for transporting hydrogen from the reaction chamber.

In some embodiments, the hydrogen generator comprises a hydrogen membrane reactor having a combustion chamber and a reaction chamber, the combustion chamber in a fluid connection with and a heat exchange relationship with the reaction chamber.

In the hydrogen membrane reactor, the combustion chamber contains a first catalyst coated substrate and reaction chamber contains a second catalyst coated substrate. In the combustion chamber, the first catalyst coated substrate includes pores and being of in the form of a metal foam, monolith or mesh or a ceramic foam or monolith, and in the reaction chamber the second catalyst coated substrate also includes pores and being in the form of a metal foam, monolith or mesh or a ceramic foam or monolith.

In some embodiments, the hydrogen membrane reactor comprises a top plate, a bottom plate, and a separation plate having first and second opposing surfaces. In the hydrogen membrane reactor, the top plate and the first surface of the separation plate together define the reaction chamber and the bottom plate and the second surface of the separation plate together defining the combustion chamber and combustion zone.

A hydrogen separation membrane having first and second opposing surfaces is included in the reaction chamber and is disposed between the top plate and the separation plate. The top plate and the first surface of the hydrogen separation membrane together define a hydrogen exhaust zone, and the separation plate and the second surface of the hydrogen separation membrane together define a reaction zone.

In the hydrogen membrane reactor, at least one of the combustion zone, reaction zone and exhaust zone housing a combustion catalyst coated porous substrate creating a fluid path through the zone.

In some embodiments, the hydrogen generator comprises a hydrogen membrane reactor having a reaction chamber and a combustion chamber, a fuel supply; at least one fuel supply line and a pre-treatment chamber.

In the hydrogen generator the fuel supply line for transporting fuel from the fuel supply to the hydrogen membrane reactor, and the pre-treatment chamber is in fluid communication with the hydrogen membrane reactor and the fuel supply line. In the hydrogen membrane reactor, the combustion chamber is in a fluid connection with and a heat exchange relationship with the reaction chamber.

In the hydrogen generator, the fuel from the fuel supply is pre-reformed to a hydrogen containing gaseous mixture in the pre-treatment chamber prior to feeding into the hydrogen membrane reactor.

In some embodiments, the hydrogen generator comprises a hydrogen membrane reactor having a combustion chamber and a reaction chamber, at least one fuel supply, a fuel supply line, an oxygen supply, an oxygen supply line, a second fuel supply line, a reaction product line, a fuel heat exchanger, and an oxygen heat exchanger.

In the hydrogen generator, the combustion chamber is in a fluid connection with and a heat exchange relationship with the reaction chamber, the reaction chamber including a reaction zone and a hydrogen exhaust zone.

In the hydrogen generator, the fuel supply line is for transporting fuel from the fuel supply to the reaction chamber, the oxygen supply line is for transporting oxygen from the oxygen supply to the combustion chamber, the second fuel supply line is for transporting fuel from the fuel supply to the combustion chamber, the reaction product line is for transporting hydrogen from the reaction chamber, the fuel heat exchanger is operably connected to the fuel supply line and the reaction tail gas line, and the oxygen heat exchanger is operably connected to the oxygen supply line and the combustion by-product line. In the hydrogen generator, at least one of the fuel heat exchanger and oxygen heat exchanger includes a porous substrate creating a path through the exchanger.

In some embodiments, the hydrogen generator comprises a hydrogen membrane reactor having a reaction chamber and a combustion chamber, a fuel supply, at least one fuel supply line, a tail gas supply line, a combustion by-product line, a reaction product line, a water supply, and a water supply line In the hydrogen reactor, the combustion chamber is in a fluid connection with and a heat exchange relationship with the reaction chamber, the fuel supply includes a hydrocarbon fuel, at least one fuel supply line is for transporting the hydrocarbon fuel from the fuel supply to the hydrogen membrane reactor, the tail gas supply line is for transporting tail gases from the reaction chamber, the combustion by-product line is for transporting combustion by-products from the combustion chamber, a reaction product line for transporting hydrogen from the reaction chamber, the water supply line is for transporting water to the hydrogen membrane reactor, the water supply line is in heat exchange relationship and fluid communication with the hydrogen membrane reactor, In some embodiments, the hydrogen generator comprises a hydrogen membrane reactor having a reaction chamber and a combustion chamber, a fuel supply, at least one fuel supply line, and a supplemental fuel supply.

In the hydrogen reactor, the combustion chamber is in a fluid connection with and a heat exchange relationship with the reaction chamber, at least one fuel supply line is for transporting fuel from the fuel supply to the hydrogen membrane reactor and the supplemental fuel is in fluid communication with combustion chamber during a start-up sequence of the hydrogen generator.

In some embodiments, the hydrogen generator comprises a hydrogen membrane reactor having a combustion chamber and a reaction chamber, a combustion by-product line, a reaction product line for transporting hydrogen from the reaction chamber, and a methanator.

In the hydrogen generator, the combustion chamber is in a fluid connection with and a heat exchange relationship with the reaction chamber, the combustion by-product line is for transporting combustion byproducts from the combustion chamber, the reaction product line is for transporting hydrogen from the reaction chamber, and the methanator in fluid communication with the reaction product line and/or the combustion product line.

According to one embodiment, a method for generating hydrogen in a hydrogen membrane reactor is disclosed. The hydrogen membrane reactor has a combustion chamber and a reaction chamber, the combustion chamber is in a fluid connection with and a heat exchange relationship with the reaction chamber, the combustion chamber includes a combustion catalyst having a combustion catalyst light-off temperature, the reaction chamber includes a separation membrane defining a reaction zone and an exhaust zone in the reactor chamber, the reaction zone includes a reaction catalyst, the reaction catalyst has a reaction catalyst light-off temperature, and the combustion catalyst has light off temperature lower than the reaction catalyst light off temperature.

The method comprises: flowing a supplemental fuel into the combustion chamber at the combustion catalyst light off temperature, the combustion of the supplemental fuel generating first combustion product gases; replacing the flowing supplemental fuel into the combustion chamber with a combustible fuel at approximately a time when the combustion catalyst's temperature reaches the combustion catalyst light-off temperature and continuing combustion to enable the temperature of the reaction catalyst to reach the reaction catalyst light off temperature, the combustion of the combustible fuel generating second combustion product gases; flowing a hydrogen-producing fuel in the reaction zone to contact the reaction catalyst to produce hydrogen gas mixture and reaction tail gases, at the reaction catalyst light off temperature; separating the hydrogen from the hydrogen gas mixture produced in the reaction zone to the exhaust zone of the reactor chamber through the hydrogen separation membrane; and collect the hydrogen gas produced from the exhaust zone of the reaction chamber.

In embodiments of the method where the hydrogen gas includes traces of CO and/or $CO_2$, collecting the hydrogen produced from the exhaust zone of the reaction chamber comprises flowing the hydrogen gas mixture through a methanator having a methanation catalyst to convert the CO and/or $CO_2$ to $CH_4$.

In some embodiments flowing a hydrogen producing fuel in the reaction zone comprises: contacting the hydrogen producing fuel with a reaction catalyst in a pre-treatment chamber containing a suitable catalyst to produce hydrogen containing product gases; and flowing the resultant hydrogen containing product gases to the reaction zone.

In embodiments where the hydrogen producing fuel is a hydrocarbon fuel, flowing a hydrogen producing fuel in the reaction zone comprises contacting a hydrocarbon fuel with water in the reaction zone to produce a reaction zone hydrogen gas mixture and tail gases, the reaction zone hydrogen gas mixture and the tail gases including water vapor. In embodiments where the hydrogen producing fuel is a hydrocarbon fuel, flowing a hydrogen producing fuel in the reaction zone can also comprise: contacting the hydrocarbon fuel with water in a pre-treatment chamber including a suitable catalyst to produce a pre-treatment chamber hydrogen containing gas mixture, and flowing the resultant pre-treatment chamber hydrogen containing gas mixture to the reaction zone, the pre-treatment chamber hydrogen containing gas mixture and the reaction tail gases including water vapor.

In embodiments where the reaction tail gases contain water vapor, the method can also comprise: condensing water vapor in the reaction tail gases by cooling and pressure reduction, obtaining condensed vapor and tail gases; routing resultant tail gases to the combustion chamber, and recycling the condensed water.

In embodiments where flowing a hydrogen producing fuel in the reaction zone comprises contacting a hydrocarbon fuel with water in the reaction zone to produce a reaction zone hydrogen gas and tail gases, the water can be preheated to about the boiling point of the hydrocarbon fuel.

In embodiments where the combustible fuel is a hydrocarbon fuel, the combustion reaction can be carried out in presence of water and the second combustion product gases includes water vapor.

In embodiments where the combustion chamber product gases comprises water vapor, the method can further comprise condensing water present in the combustion chamber product gases by heat exchange with the incoming air to the combustion chamber; recycling the water to the water supply; and venting the cooled combustion chamber product gases to the atmosphere.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE INVENTION

Figure 1:
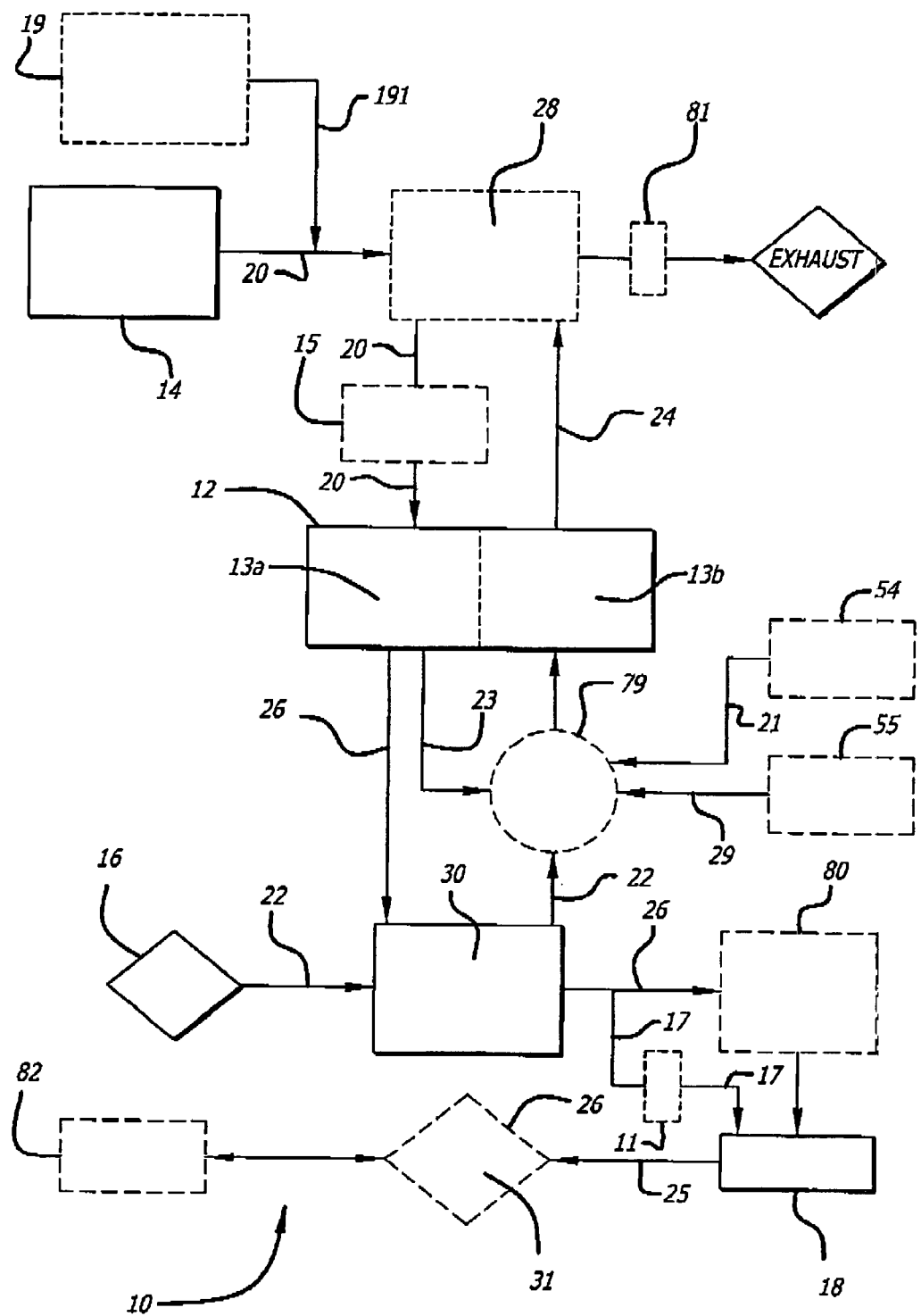
FIG. 1 is a block diagram illustrating the primary components of a hydrogen generator in accordance with the present invention.

Particular embodiments of the invention are described below in considerable detail for the purpose for illustrating its principles and operation. However, various modifications may be made, and the scope of the invention is not limited to the exemplary embodiments described.

The hydrogen generators in accordance with the invention include a reaction chamber and a combustion chamber. In the reaction chamber hydrogen is produced from a fuel. In the combustion chamber thermal energy is produced by combustion of a fuel, wherein the thermal energy produced is to be supplied to the reaction chamber. Accordingly, the reaction chamber and the combustion chamber are in a heat exchange relationship.

The fuel to be supplied to the reaction chamber include a wide variety of chemically different fuel, such as hydrocarbons and ammonia.

It is an advantage of the hydrogen generators in accordance with the invention, that with only minor modifications they can be used to generate hydrogen from either ammonia or hydrocarbon fuels. In embodiments wherein the hydrogen generator employs ammonia as fuel, the hydrogen is generated by ammonia decomposition. In embodiments wherein the hydrogen generator employs hydrocarbons as fuel, the hydrogen is generated by hydrocarbon cracking reaction, in particular in the form of partial oxidation or steam reformation. Representative hydrocarbon fuels include, methanol, propane, butane, gasoline, and kerosene fuels, such as JP-8. With fuels containing contaminants such as sulfur (as found in JP-8), the sulfur may be removed from the fuel before feeding into the hydrogen membrane reactor.

In the reaction chambers and in the combustion chamber the fuel is preferably processed in presence of a catalyst. The catalyst used in the reaction chamber may be different from the catalyst used in combustion chamber.

In some embodiments, the fuel provided to the reaction chamber is the same provided in the combustion chamber. In those embodiments, the fuel must be capable of both generating hydrogen and providing thermal energy. In other embodiments the fuel supplied to the reaction chamber is different from the fuel supplied to the combustion chamber and so can be the catalyst.

In preferred embodiments, the fuel is a liquid fuel. For example, while ammonia is a gas at standard temperature and pressure (STP) conditions, the ammonia is preferably stored in a liquid state. The ammonia is easily liquefied by compression (114 pounds per square inch) and/or by cooling to about −33° C. Similarly, while liquid hydrocarbons are available, the use of a liquid hydrocarbon fuel greatly simplifies fuel transport. As with ammonia, hydrocarbons that are gaseous at STP (such as propane) are conventionally stored and transported as liquefied gases. Consequently, in preferred embodiments, the fuel is either a material that is a liquid at STP or a liquefied gas.

The hydrogen generator should preferably incorporate a relatively small, efficient hydrogen membrane reactor characterized by having excellent heat and mass transfer rates, and adapted to operate at a relatively low reaction temperature (so that conventional materials can be used for fabricating reactor components). The reactor includes two chambers, a reaction chamber, followed by a combustion chamber. The two chambers are arranged in close proximity and are in a heat exchange relationship with one another. A hydrogen separation membrane is in fluid communication with the hydrogen generating reaction chamber. Each chamber preferably incorporates highly active catalysts characterized by having rapid residence times and excellent heat transfer abilities with respect to the reactor (to enable a minimal volume reactor to be employed). The system further includes a pair of lightweight recuperative heat exchangers characterized as having meso-dimensioned channels and very high heat transfer rates, as well as extremely efficient insulation that minimizes reactor and heat exchanger heat loss into the environment.

A fuel supply is provided, as well as an oxygen supply, e.g., an ambient air intake, and an exhaust. In some embodiments, a fuel supply containing fuel to be provided to both the reaction chamber and the combustion chamber is included. In other embodiments, two or more fuel supplies are associated with the hydrogen generator, and in particular a first fuel supply containing fuel to be supplied to the reaction chamber and a second or additional fuel supply containing the fuel to be supplied to the combustion chamber.

A supply line connects each supply to the chamber where the content of the supply is to be provided. Also a combustion by-product line and a tail gases supply line are provided to respectively transport by-products from the combustion chamber and reaction chamber. A reaction product line is provided for transporting the hydrogen produced in the reaction chamber.

The hydrogen produced can be routed to an optional PEM fuel cell, a storage tank or other hydrogen using apparatus. Hydrogen fuel generators employing ammonia as the reaction fuel may further incorporate an ammonia adsorbent supply in fluid communication with a hydrogen reaction product line exiting the hydrogen membrane reactor to remove trace ammonia that could poison a fuel cell or have an adverse effect on the fuel cell. Hydrogen fuel generators employing ammonia as the combustion fuel may further incorporate an ammonia adsorbent supply in fluid communication with a combustion by-product line exiting the hydrogen membrane reactor to trap any ammonia that may exit the chamber. Hydrocarbon fueled embodiments preferably include a water storage tank, a water/fuel pump, an ambient air pump, and optionally a steam recovery vessel and/or a methanator.

Both hydrocarbon fueled embodiments and ammonia fueled embodiment can include also a pre-reformation or pre-treatment chamber chamber, a hydrogen reservoir, a supplemental fuel supply and relevant supply line to be used to light-off the combustion catalyst, and a storage metal hydride container containing hydrogen.

By minimizing component size, a larger proportion of the system can be dedicated to the volume of fuel ammonia supplied, thereby increasing the amount of hydrogen that can be generated for each tank of ammonia fuel.

FIG. 1 shows an exemplary hydrogen generator 10. The hydrogen generator includes a hydrogen membrane reactor 12 having two separate chambers, a reaction chamber 13a in a heat exchange relationship with a combustion chamber 13b (also shown in FIGS. 2-4), a fuel supply 14, an oxygen supply 16, and a hydrogen reservoir 18. The hydrogen generator 10 can optionally include a second fuel supply 54, a supplemental fuel supply 55, a pre-reformation chamber 15, and a methanator 11, reported in the schematic representations with broken lines.

In FIG. 1, appropriate fluid lines are included as shown, and arrowheads incorporated into such fluid lines indicate the proper flow of fluid through the hydrogen generator. The fluid lines include a fuel supply line 20 for transporting fuel from the fuel supply 14 to the reaction chamber 13a, an oxygen supply line 22 for transporting oxygen from the oxygen supply 16 to the combustion chamber 13b, a tail gas supply line 23 for transporting tail gases from the reaction chamber 13a and directly or indirectly into the combustion chamber 13b, a combustion byproduct line 24 for exhausting the combustion by-products from the combustion chamber, and a reaction product line 26 for transporting hydrogen from the reaction chamber 13a to the hydrogen reservoir 18. The fluid lines also optionally include second fuel supply line 21 for transporting fuel from the second fuel supply 54 directly or indirectly to the combustion chamber 13b, the supplemental fuel supply line 29, for transporting the supplemental fuel from the supplemental fuel supply 55 to the combustion chamber 13b, in a start-up phase when a start-up sequence is utilized.

The fuel for the combustion chamber 13b can be provided by the first fuel supply 14 and/or by the second supply 54. The fuel to the combustion chamber 13b from fuel supply 14 can be provided through the tail gas supply line 23, which in those embodiments also as a second or additional fuel supply providing the fuel from the fuel supply 14 to the combustion chamber 13b. While the tail gas supply line is shown external to the reactor, in some embodiments, the tail gas supply line is placed within an insulated region inside the reactor, so that heat loss does not occur as the tail gas is transported from the reaction chamber 13a to combustion chamber.

Especially in embodiments where a maximum energy density is desired, proper management of thermal energy is critical. Fuel in the fuel supply 14 is used both to provide the thermal energy needed to drive the hydrogen-production reaction, as well as a feedstock in the reaction. Thus, every gram of fuel used to generate thermal energy is a gram that is unavailable to be used as feedstock. If less feedstock is available, the energy density of the system is reduced. Accordingly, in some embodiments, a fuel heat exchanger 28 and an oxygen heat exchanger 30 are employed to make efficient use of the thermal energy available to the system. In some embodiments, the hydrogen membrane reactor 12, the fuel heat exchanger 28, and the oxygen heat exchanger 30, are all integrated into a single component.

The fuel heat exchanger 28 is disposed in the fuel supply line 20 and in the combustion by-products supply line 24 to provide a thermal connection between the fuel and the combustion by-products. The oxygen heat exchanger 30 is disposed in the oxygen supply line 22 and the reaction products line 26 to provide a thermal connection between the oxygen and the reaction products. The fuel heat exchanger extracts heat from the hot combustion by-product gases exiting combustion chamber and preheats the fuel entering the reactor. Similarly, the oxygen heat exchanger extracts heat from the hot reaction product gases exiting hydrogen membrane reactor and preheats the oxygen entering the reactor.

In an alternative embodiment, the fuel heat exchanger 28 is disposed in the reaction tail gas line 23 to provide a thermal connection between the fuel and the reaction tail gases, while the oxygen heat exchanger 28 is disposed in the combustion by-products line 24 to provide a thermal connection between the oxygen and the combustion by-products. With both embodiments, the materials entering the hydrogen membrane reactor 12 are preheated to temperatures approaching the operating temperature of the reactor, so that additional fuel is not consumed to heat the reactants.

The fuel and oxygen heat exchangers 28 and 30 are preferably counterflow-type heat exchangers. In some embodiments, the heat exchanges are shell-and-tube type devices (see below description of FIGS. 4A and 4B). In other embodiments, the heat exchangers are stacked plate-type heat exchangers (see below description of FIG. 5). Both heat exchangers may be insulated, so that little thermal energy is lost.

In those embodiments where the fuel is a liquefied gas such as ammonia or propane, stored under pressure, no pumping system is required to the fuel through fuel supply line 20, through the fuel heat exchanger 28, and into the hydrogen membrane reactor 12. However, in embodiments where the fuel is a liquid such as JP-8 a separate pumping system (not shown) must be employed.

The hydrogen generator 10 can include a pre-reformation chamber 15. The pre-reformation chamber can be included in particular configurations of the hydrogen generator wherein fuel which is pre-reformed to a hydrogen containing gaseous mixture prior to feeding into the reaction chamber. In one embodiment, such pre-reformation can be realized by incorporating a suitable catalyst in the pre-reformation chamber 15 that is preferably in a heat exchange relationship with the combustion chamber. For example, in one configuration, the combustion chamber can be sandwiched between the reformer chamber and the pre-treatment chamber chamber. In another configuration, a portion of the reformer chamber that is close to the feed inlet can be membrane-less and constitute the pre-treatment chamber chamber.

In another embodiment the pre-reformation is realized by incorporating a suitable catalyst in a hot zone of the fuel supply line, such as a portion of the feed supply line that is close to the reformer chamber, or a portion of the feed supply line that is intentionally contacted with the hot surfaces of the hydrogen generator.

In still other embodiments, an exemplary hydrogen generator utilizing pre-reformation utilizes a suitable catalyst incorporated in a pre-reformation chamber that constitutes a membrane-less portion located at an entrance of the membrane reformer.

The hydrogen generator 10 can also include a second or additional fuel supply 55 and an associated additional fuel supply line 21 for transporting the fuel to the combustion chamber 13b. The additional fuel supply line 21 to the combustion chamber 13b is in fluid communication with the oxygen supply line 22 to the combustion chamber.

In particular configurations, wherein a supplemental fuel is used in a start-up sequence, the additional fuel supply line 21 in fluid connection with the combustion chamber 13b is also in fluid communication with a supplemental fuel supply 55 and/or the related supplemental fuel supply line 29. In one embodiment the supplemental fuel is hydrogen. In this embodiment, hydrogen is compressed and stored in metal hydride materials, which constitute the supplemental fuel supply 55. Such compression is preferably effected using hydrides and heat from the hydrogen generator.

The hydrogen generator 10 can also include an air injector pump 78 disposed in the oxygen supply line 22 between the oxygen heat exchanger 30 and the hydrogen membrane reactor and in the tail gas supply line 23. The injector pump conveys both the tail gas exiting the reaction chamber and the air from the oxygen supply into the combustion chamber of hydrogen membrane reactor 12. Alternately, air can be transferred to the combustion chamber using a suitably sized blower, while the fuel is mixed with air in a manner to prevent undesirable auto-ignition prior to entry into the combustion chamber.

The hydrogen generator 10 can further comprise a methanator 11 in fluid communication with the reaction product line 26. In particular embodiments, the methanator is preferably operated below 200° C. The methanator is typically located in the reaction product line 26 so as to be exposed to temperature of about 200° C. or lower. In embodiments, a safety system associated with the methanator 11 is further included, which upon a temperature spike in the methanator, caused by increased amounts of CO and $CO_2$ in the hydrogen product due the formation of defects in the membrane or membrane failure, is used to shut-down the system in a safe manner and to isolate the hydrogen generator from the fuel cell.

The hydrogen exiting the methanator can be conducted into a hydrogen reservoir, such as the hydrogen reservoir 18, through a methanator line 17. Additionally, or in alternative this hydrogen can be compressed and stored in metal hydride materials, which in embodiments wherein the hydrogen is used as a supplemental fuel in a start-up procedure can also be such as the supplemental fuel supply 55. Such compression is preferably effected utilizing hydrides and heat from the hydrogen generator. The resultant stored hydrogen can be utilized for the cold start-up.

In other embodiments the hydrogen exiting the methanator 11 can be conducted into a fuel cell.

Preferably, the hydrogen generator 10 will generate hydrogen on demand and in those embodiments where the hydrogen is to be used immediately after it is generated the hydrogen reservoir 18 is not required. However, there are inefficiencies inherent in a hydrogen generating cycle that comprises a series of short periods of operation followed by long periods of inactivity, because during the start up phase, the fuel is being used to bring the system up to an operating temperature rather than for generating hydrogen. Therefore, in some embodiments, the hydrogen reservoir 18 is employed to store hydrogen not currently required, so that while the system is at operating temperature, the fuel can be employed to generate hydrogen for later use, rather than to bring the system to operating temperature.

While the hydrogen reservoir 18 can be an empty vessel that acts as a buffer to even out fluctuations in the hydrogen supply, it may be advantageous to route some of the hydrogen to a storage containing metal hydride materials that can store hydrogen. Compression of hydrogen (hydrogen product gas exits the exhaust zone at close to ambient conditions) and storage of hydrogen can be effected using hydrides as exemplified and obtainable from Hera Hydrogen Storage Systems (Quebec, Canada). Typically metal hydrides are composed of complexes of elements such as Lanthanum, Aluminum, nickel, boron, Lithium, magnesium. Hydrogen stored in the reservoir can be used for light-off of the combustion catalyst during start-up.

In embodiments where the fuel is a hydrocarbon fuel a water tank 19 can be included in the system with a water supply line 191 for transporting the water to the heat exchanger 28 and/or fuel supply line 20.

In those embodiments employing ammonia as a fuel and where the hydrogen gas is to be used to power an H/AFC (PEM fuel cell), it is preferred to include an ammonia adsorbent supply 80 in fluid connection with the reaction product line 26. H/AFCs can be adversely affected by even trace amounts of ammonia, so the adsorbent is capable of removing any residual ammonia contained within the hydrogen exiting hydrogen membrane reactor 12. Under ideal conditions, a properly designed and functioning hydrogen membrane reactor will not allow any ammonia to pass through the membrane. However, microscopic manufacturing defects, post manufacture punctures, or poor sealing along the edges of a hydrogen membrane can enable a small amount of ammonia to contaminate the hydrogen stream.

In embodiments where the hydrogen is used for purposes that are not as sensitive to residual ammonia, such as welding or metal treating, the absorbent supply may not be necessary. Similarly, if manufacturing defects, punctures, and sealing deficiencies are uncommon, then ammonia adsorbent supply will not be required.

An ammonia adsorbent supply 81 can also be included in fluid connection with the combustor chamber exhaust line 24 to trap any ammonia that may exit the chamber, particularly when ammonia is used for light-off of the combustion catalyst during the start-up sequence.

The adsorbent within the adsorbent supply 81 should remove substantially all (leaving less than 1 ppm) of the residual ammonia from the hydrogen product. Preferred adsorbents include carbon and modified carbon adsorbents. Most preferred adsorbents include carbon whose surface has been impregnated to include bound acid molecules. The acid thus bound neutralizes the residual ammonia. At a minimum, the most preferred adsorbent has 2 millimoles of strong acid adsorption sites per gram of carbon, and the most preferred adsorbent can have up to 5 millimoles per gram of carbon.

The hydrogen generator 10 can be used to generate hydrogen to be used in an H/AFC fuel cell 31, even if such the hydrogen generator 10 can be beneficially employed to generate hydrogen for other purposes as well. For example, the generator can be used as a source of hydrogen for welding or metal treating. Thus, the fuel cell 31 is shown as an optional component.

For embodiments in which the fuel cell 31 is added to the system to generate electricity from the hydrogen produced, the preferred fuel cell is a PEM (H/AFC) fuel cell. Embodiments that incorporate a battery 82 are also contemplated. Such systems can provide useful power even when no oxygen is available. Normally, oxygen is required by the hydrogen generator 10 to react with the fuel in the combustion chamber of the hydrogen membrane reactor 12. Oxygen is also needed as a fuel for the reaction that occurs in the fuel cell 31. However, in some embodiments, the system first can be operated in an aerobic environment for a period of time sufficient to generate sufficient hydrogen for the fuel cell to produce enough electricity to bring the battery to a substantially charged state. Then the system can be placed in an anaerobic environment (such as underwater) and still be capable of supplying electrical power from the battery for a period of time. Note that the incorporation of batteries increases the system size and weight, and somewhat decreases the energy density of the system; accordingly, this embodiment is most beneficially employed when anaerobic conditions are anticipated. Preferably, such a system will be prepared for use with a fully charged battery and a full fuel supply 14, so that fuel from the fuel supply does not need to be used to initially charge the battery.

In general, the physical size of each of the functional elements of a hydrogen generator in accordance with the invention depends on the desired size and capacity of the hydrogen generator. In one preferred embodiment, the hydrogen generator is less than 1 liter in volume and 1 kilogram in mass. In such an embodiment, the individual size of each element is critical in obtaining a hydrogen generator that is sufficiently compact. In other embodiments, the exact size of the system is not critical, though a compact design is typically to be preferred. In general, the size of components such as the fuel supply 14 and the hydrogen reservoir 18 will be a function of the amount of power required and a maximum desired time interval between replenishing system consumables. For example, the fuel supply must provide a sufficient quantity of fuel to ensure that performance goals for the intended period of operation are achieved.

With respect to the hydrogen membrane reactor 12, the fuel heat exchanger 28, and the oxygen heat exchanger 30, these elements are preferably as compact and light-weight as practical. Especially for embodiments in which the overall system size is of concern, minimizing the size and weight of the hydrogen membrane reactor, the fuel heat exchanger, and the air heat exchanger enables a greater proportion of system size and weight to be dedicated to fuel storage, thereby increasing the energy density and/or operating interval between refueling of the system.

It should be understood that while in at least one embodiment of the present invention, a preferred reactor will be fabricated as small and compact as feasible, hydrogen membrane reactors in accordance with the present invention can be scaled up to a larger size capable of generating significantly larger volumes of hydrogen, if desired. Similarly, such an exemplary hydrogen membrane reactor can be employed in hydrogen generating systems using large fuel supplies, to achieve a hydrogen generator that can provide modest volumes of hydrogen to a fuel cell (or other apparatus) for extended periods of time.

Figure 2:
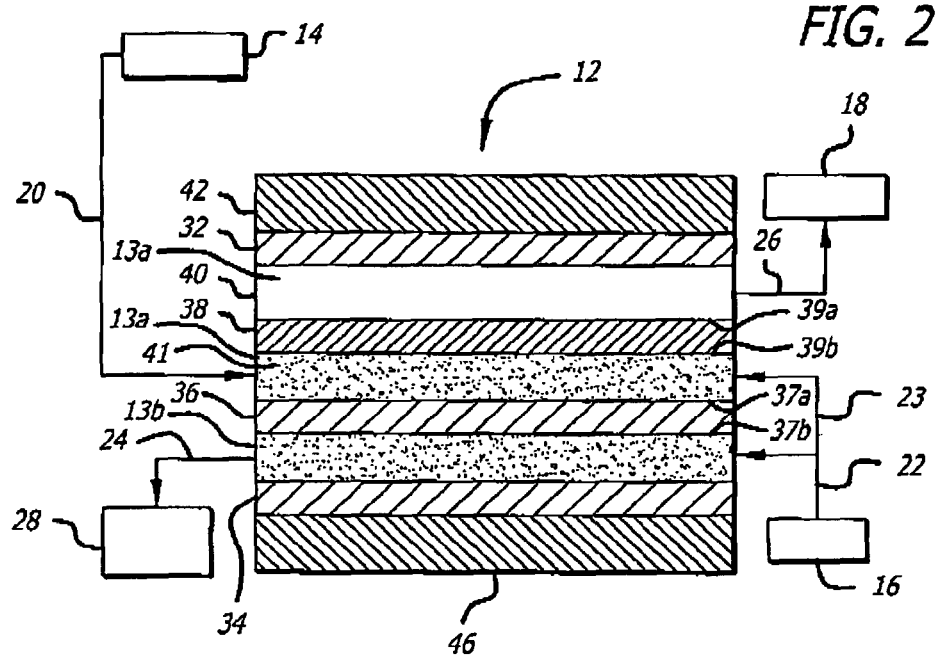
FIG. 2 is a schematic view of a hydrogen membrane reactor and related components for use in accordance with the present invention.

FIG. 2 shows some of the features of a preferred embodiment of the hydrogen membrane reactor 12 of FIG. 1. The reactor includes a top plate 32, a bottom plate 34, and a separation plate 36 having first and second opposing surfaces 37a and 37b, respectively. The top plate and the first surface of separation plate together define the reaction chamber 13a, while the bottom plate and the second surface of the separation plate together define the combustion chamber 13b.

The separation plate 36 is preferably a thin metal plate having a high thermal conductivity. High thermal conductivity is critical, as heat generated within the combustion chamber must be available to provide the required temperature conditions within the hydrogen generating reaction chamber 13a. The top plate 32 and the bottom plate 34 are structural and not necessarily thermally conductive.

Disposed between the top plate 32 and the separation plate 36 is a hydrogen separation membrane 38. The hydrogen separation membrane enables the hydrogen to be separated from the other decomposition or reformation reaction products. Such membranes allow hydrogen to diffuse across (through) the membrane, while preventing the other reaction products from crossing the membrane. Such membranes are commercially readily available or can be prepared by depositing such membranes on porous substrates.

The hydrogen separation membrane 38 has first and second opposing surfaces 39a and 39b, respectively, spanning the width of the reactor. The top plate 32 and the first surface together define a hydrogen exhaust zone 40, while the separation plate 36 and the second surface together define a reaction zone 41.

In an alternative embodiment, a hydrogen separation membrane 38 that is substantially smaller hydrogen separation membrane is employed. When ammonia is used as the fuel, contact with the pure ammonia can shorten the life of the hydrogen separation membrane 38. Therefore, in some embodiments the membrane is not placed where the ammonia first enters the hydrogen membrane reactor 12. In such embodiments, the hydrogen membrane includes a non-membrane leader portion of a suitable length to ensure that the product gas inside the reactor first contacts the membrane only after the ammonia concentration in the reactor has been reduced to ppm levels. For example, in a generator designed to provide sufficient hydrogen to generate 20 watts of power, a palladium membrane with less than about 5 $cm^2$ of membrane is sufficient to efficiently separate hydrogen from the product gas. In this alternative embodiment, there is a single hydrogen exhaust channel in fluid communication with the relatively small membrane surface.

The top plate 32 separates the hydrogen exhaust zone 40 from an insulating panel 42, while the bottom plate 34 separates the combustion chamber 13b from an insulating panel 46.

Figure 3:
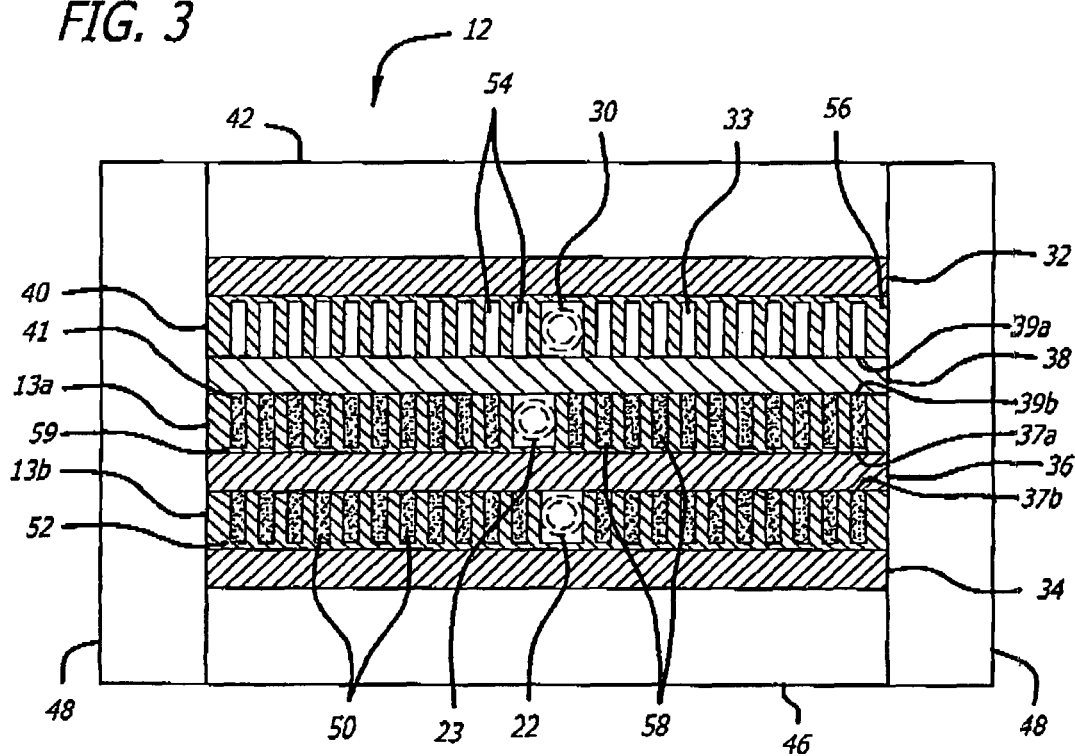
FIG. 3 is a cross-sectional view of a hydrogen membrane reactor in accordance with the present invention.
Figure 4:
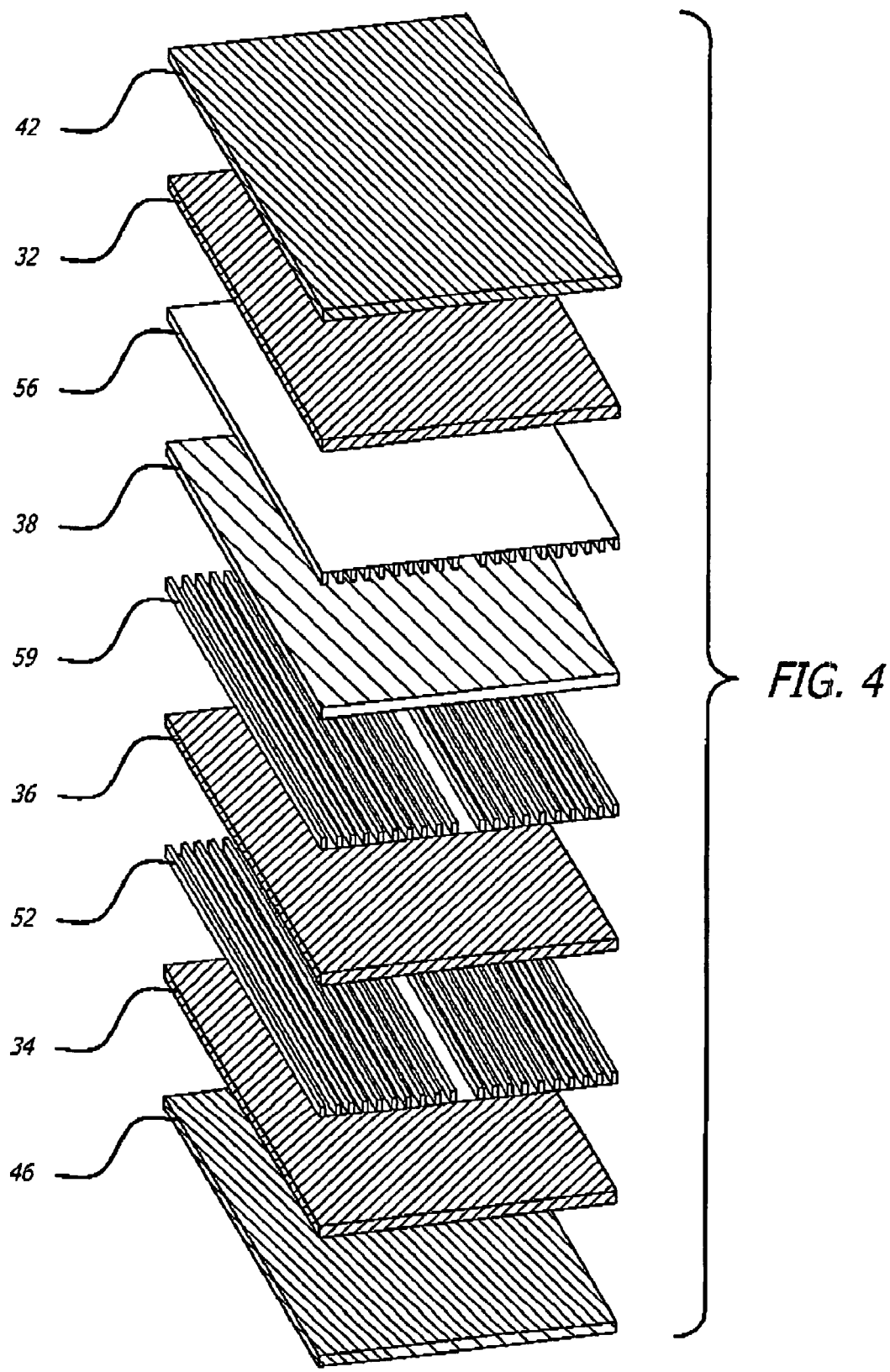
FIG. 4 is an exploded isometric view of the different layers of the hydrogen membrane reactor of FIG. 3.

FIG. 3 is a cross-sectional view of a preferred embodiment of the hydrogen membrane reactor 12. In the preferred embodiments of FIG. 3, the sides of the reactor are insulated, with insulating side panels 48 as well as the top and the bottom of the reactor insulated with insulating panels 42 and 46, respectively. Preferably, the insulating panels are fabricated from an aerogel material, which can provide excellent insulation and is a very lightweight material. FIG. 4 is an exploded isometric view of the different layers of the hydrogen membrane reactor of FIG. 3, with the side insulative layers omitted for clarity.

FIGS. 3 and 4 illustrate a plurality of combustion channels 50 extending radially from the adjacent surface 37b of the separation plate 36, the combustion channels creating a fluid path through the combustion chamber. The combustion channels are formed in a thin metal combustion plate or sheet 52 interposed between the bottom plate 34 and the separation plate.

A plurality of hydrogen exhaust channels 54 extending radially from the first surface 39a of the hydrogen membrane 38 are formed in a thin perforated metal hydrogen exhaust channel plate or sheet 56 interposed between the top plate 32 and the hydrogen membrane. The hydrogen exhaust channels 54 extend radially from the top plate, creating a fluid path through the hydrogen exhaust zone. The perforations are typically 10 to 1000 microns in size and more preferably between 500 to 2000 microns in size and preferably set-up apart equidistant from each other to provide a flow volume (or porosity) of at least 30%.

A plurality of reaction channels 58 extending radially from the second surface 39b of the hydrogen membrane are formed in a thin perforated metal reaction channel plate or sheet 59 interposed between the bottom plate 34 and the separation plate, creating a fluid path through the reaction zone. In preferred embodiments, these channels are formed in the thin metal sheets, either by micromachining or stamping. It should also be understood, that the specific orientation and configuration of mesochannels in any of these elements is not critical, so long as for the orientation selected, the efficiency and processing benefits provided by mesochannels are retained (i.e., small-dimensioned fluid channels that provide excellent fluid flow and high heat transfer rates).

In other embodiments, mesochannels can be incorporated on either side of the separation plate to exploit better heat transfer rates. Also the mesochannels can be incorporated on the top and bottom plates that would obviate the need for forming the mesochannels on separate perforated sheets that are attached or support to the membrane. Modifying the separation plate and the end plates (top and bottom) to provide mesochannels on the separation and end plates, can also lead to a reduction in fabrication costs.

The dimensions of the channels 50, 54, and 58 within the hydrogen membrane reactor are preferably "meso" in scale. Meso scale systems fall between the macro scale systems associated with traditional full-sized systems, like those used in the petrochemical industry, and the micro scale systems commonly encountered in the microelectronics industry. That is, preferably the height and or width of each channel is between 0.01 mm and 10 mm, and is more preferably between 0.5 mm and 5 mm.

In a preferred embodiment, the mesochannel fluid flow dimensions to enhance heat transfer and reaction rates are incorporated not by machining such channels into components such as the separation plate, end plates etc, but by incorporating a porous substrate possessing the said fluid flow dimensions in the mesoscale range, and wherein the porous substrate is in intimate contact with the metal surfaces that define the reaction chamber, the combustion chamber and the hydrogen exhaust zone. In those preferred embodiments the metal combustion plate or sheet 52, the metal hydrogen exhaust channel plate or sheet 56 and the metal reaction channel plate or sheet 59 are made of a porous substrate. It is preferable to use porous metal substrates to enhance heat transfer rates from the combustion chamber to reaction chamber and to the hydrogen exhaust zone. Porous metal substrates can be in the form of foams, meshes or felts. Suitable candidates of porous metal foam substrates are the fully sintered, open cell reticulated/foam substrates that are supplied by Porvair, Inc (Hendersonville, S.C.). For example metal substrates with a pore size of 10 to 40 pores per inch (PPI) offer pore diameters and therefore flow dimensions that are in the mesoscale range of 0.5 mm to 2.0 mm. Such porous metal foams are available in materials that include but are not limited to FeCrAlY, Inconel® 625 and Stainless Steel 316. Inconel® 625 has a nominal composition of: Ni (+Co) 62.6 C 0.05, Mn 0.55, Fe 6.85, S 0.007, Si 0.35, Cu 0.05, Cr 20, Al 0.15, Ti 0.3, Cb(+Ta) 3.95.

Exemplary porous metal foams are formed by applying a metal coating onto a reticulated precursor, followed by thermal treatment to destroy the precursor and sintering of the metal substrate thereby providing a rigid structure. Therefore, if the reticulated precursor contains channel-like protrusions that extend from a base, then the resulting metal foam would also contain channel like features. Foams with such additional features can be utilized to further enhance heat transfer rates and surface area available when such foams are utilized for supporting a catalyst coating, for example.

Regardless of which fuel is employed, thermal energy is required to drive the desired reaction. One way of reducing the thermal energy required to drive the hydrogen generating reactions is to include an appropriate reaction catalyst within the hydrogen membrane reactor 12. Thus, in preferred embodiments, the reaction zone 41 includes a reaction catalyst to facilitate the chemical transformation of fuel into hydrogen. When mesochannel architecture in the reaction chamber 13a is realized by incorporating porous metal foam substrates with flow dimensions in the mesoscale range, then that porous metal foam substrate needs to be coated with a suitable catalyst that can reform fuels to produce hydrogen. In general, the catalysts are reaction specific, and the selection of the particular catalyst to be employed will be based, in part, on whether the selected fuel is ammonia or a liquid hydrocarbon.

Moreover, the characteristics of specific catalysts (and any required catalyst support, such as alumina) affect the design of the reactor. For example, for a given volume, different catalysts will require different flow rates to achieve the same conversion efficiency. Similarly, for a given flow rate, different catalysts will require different reactor volumes to achieve the same conversion efficiency.

Also, useful reaction catalysts function under different temperature conditions, each catalyst having a characteristic "light-off" temperature (a minimum required temperature below which little or no catalytic activity is observed), as well as a characteristic optimal temperature. These temperature parameters affect a specific reactor design by defining minimum and optimum reactor temperatures. Thus, the catalyst selected will influence optimal temperature conditions, flow rates, and reactor volumes.

The temperature conditions, in particular, determine the type of materials that can be used in fabricating the reactor (conventional metals for temperatures less than 650° C., or refractory metals for higher temperatures). Relatively low temperature reactors (operating at less than 650° C.) and appropriate catalysts are a particularly useful and preferred combination.

An example for reaction catalysts for ammonia disassociation at temperatures less than 650° C. include ruthenium-based catalysts, often provided as ruthenium dispersed in an aluminum oxide support matrix, such as Type 146, available from Johnson Matthey. By utilizing a reactor temperature of less than 650° C., very high surface area catalyst substrates, such as gamma alumina and nanophase titania can be employed. Temperatures in excess of 800° C. often cause these materials to sifter or undergo phase changes that result in a much lower substrate surface area and correspondingly lower catalyst activity. Preferably, the ruthenium ammonia disassociation catalyst is dispersed in either a gamma alumina or nanophase titania matrix when a packed catalyst bed is utilized.

Since oxygen is included with the ammonia to support the initial combustion, in some embodiments catalysts less oxygen sensitive than ruthenium-based catalysts are employed. Moreover, when assembling reactors containing oxygen-sensitive catalysts (i.e., by brazing the top cover to the reactor core) it may be beneficial to provide a reducing atmosphere in order to prevent the catalysts from oxidizing.

Nickel-based catalysts, such as Katalco 27-7™ (available from ICI/Katalco of the UK) are also preferred ammonia dissociation catalysts. However, the nickel catalyst requires a longer residence time than the ruthenium catalyst to achieve similar conversion efficiency. The ruthenium catalyst has a residence time that is approximately one-tenth that of the nickel catalyst.

Other suitable ammonia dissociation catalysts include iron oxide, rhodium, iridium, palladium, platinum and rhenium catalysts or formulations that comprise these elements.

Preferred embodiments additionally contain a combustion catalyst within the combustion chamber 13b. The combustion catalyst is employed to enable fuel to be more readily combusted to generate the thermal energy required to drive the hydrogen generation reaction. Catalytic combustion is a unique chemical reaction differing from open flame combustion, in that a catalyst is used to ensure an efficient combustion process occurs at a lower temperature. Catalytic combustion is therefore relatively safer than open flame combustion.

In particular, without such a combustion catalyst, ammonia is difficult to ignite and sustain combustion in air. For this reason, a combustion catalyst is required to enable ambient air to be employed when ammonia is used as the fuel. Preferred ammonia combustion catalysts include platinum-rhodium alloys. Similarly, by introducing platinum into a hydrocarbon/oxygen combustion process, it is possible to increase the percentage of fuel burned from less than 85% to about 98%.

The catalysts can be incorporated by any suitable method. For example, the catalysts included in reaction channels 58 and combustion channels 50 can either be incorporated as packed beds in each channel, or as a thin layer or coating deposited on the internal surfaces of the thin metal sheet comprising the channels. In a manner similar to the use of porous metal substrates in the reaction chamber, mesochannel architecture in the combustion chamber can also be realized by incorporating porous metal substrates with flow dimensions in the mesoscale range, as described previously. In this embodiment, the porous metal substrate is coated with a suitable catalyst that can catalytically combust fuels to generate heat.

Any suitable means can be employed to trigger the combustion reaction. In a preferred embodiment, a glow plug (not shown) is used. The glow plug is essentially a nichrome or other metallic element that is in contact with the combustion catalyst in the combustion chamber of the hydrogen membrane reactor 12. A small battery (not shown) delivers current to the wire, which increases the temperature of the combustion catalyst to a "light-off" temperature, i.e., to that temperature at which the ammonia combustion catalyst will facilitate the combustion of ammonia. In an alternative embodiment, a spark-based igniter is used. While the spark-based igniter offers the advantage of not requiring a battery, the air/fuel mixture must be much more tightly controlled to enable spark-based ignition to occur. Once the combustion is initiated, the process is self sustaining as long as there is sufficient fuel and oxygen, and as long as the temperature remains above 650° C.

An alternative method for starting the combustion reaction involves the use of hydrogen as the fuel during start-up. Small amounts of hydrogen can be stored in metal hydrides and used for initiation of the combustion reaction. Hydrogen is a unique fuel in that light-off can realized at room temperature using catalyst formulations that contain palladium. This practice therefore obviates the need for glow plugs, igniters etc and enhances the reliability of ignition. Once the combustion catalyst temperature reaches a range of about 200 to 300° C., the hydrogen can be replaced with a hydrocarbon fuel. The hydrocarbon fuel to the combustor can be the same or different from the fuel that is fed to the reaction chamber.

Figure 4A:
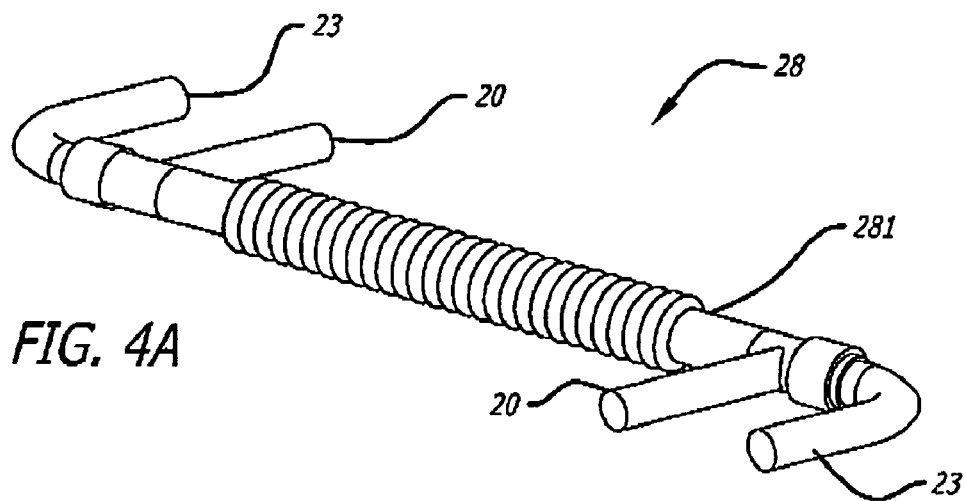
FIG. 4A is a perspective view of a heat exchanger to be operably connected to the fuel supply line and the tail gas line.
Figure 4B:
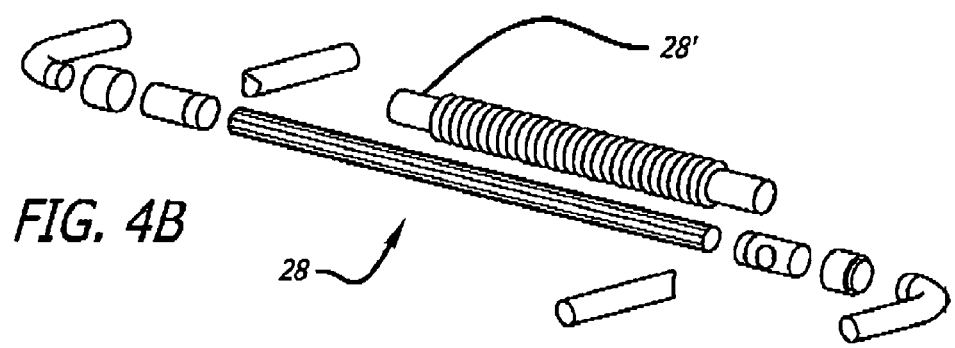
FIG. 4B is an exploded perspective view of the heat exchanger of FIG. 4A.
Figure 4C:
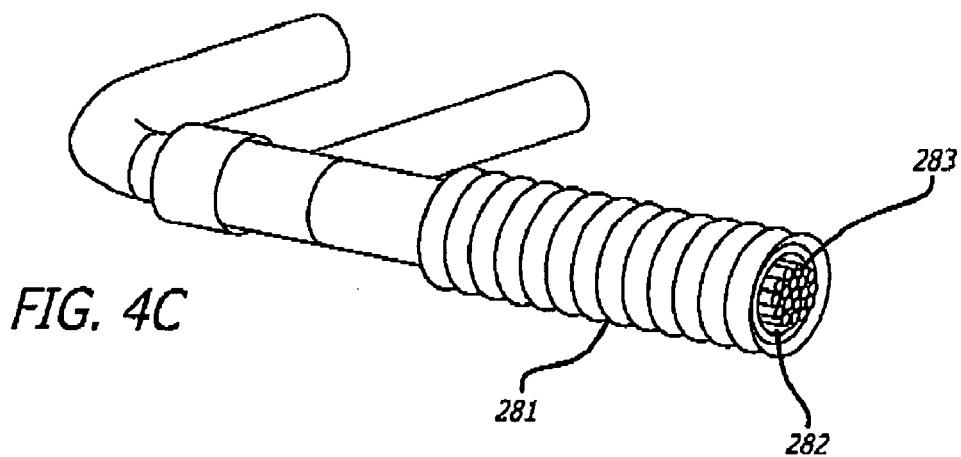
FIG. 4C is a perspective view of a portion of the heat exchanger of FIG. 4A.

The fuel and oxygen heat exchangers 28 and 30 are preferably counterflow-type heat exchangers. In some embodiments, the heat exchanges are shell-and-tube type devices. FIGS. 4A, 4B and 4C show perspective views of a shell-and-tube heat exchanger 28 which includes a shell 281 and channels 282 and 283. In the heat exchanger 28 fuel is introduced in channels 282 through the fuel supply line 20, and the tail gases are introduced in channels 283, with channels 282 not in fluid communication with channels 283.

Figure 5:
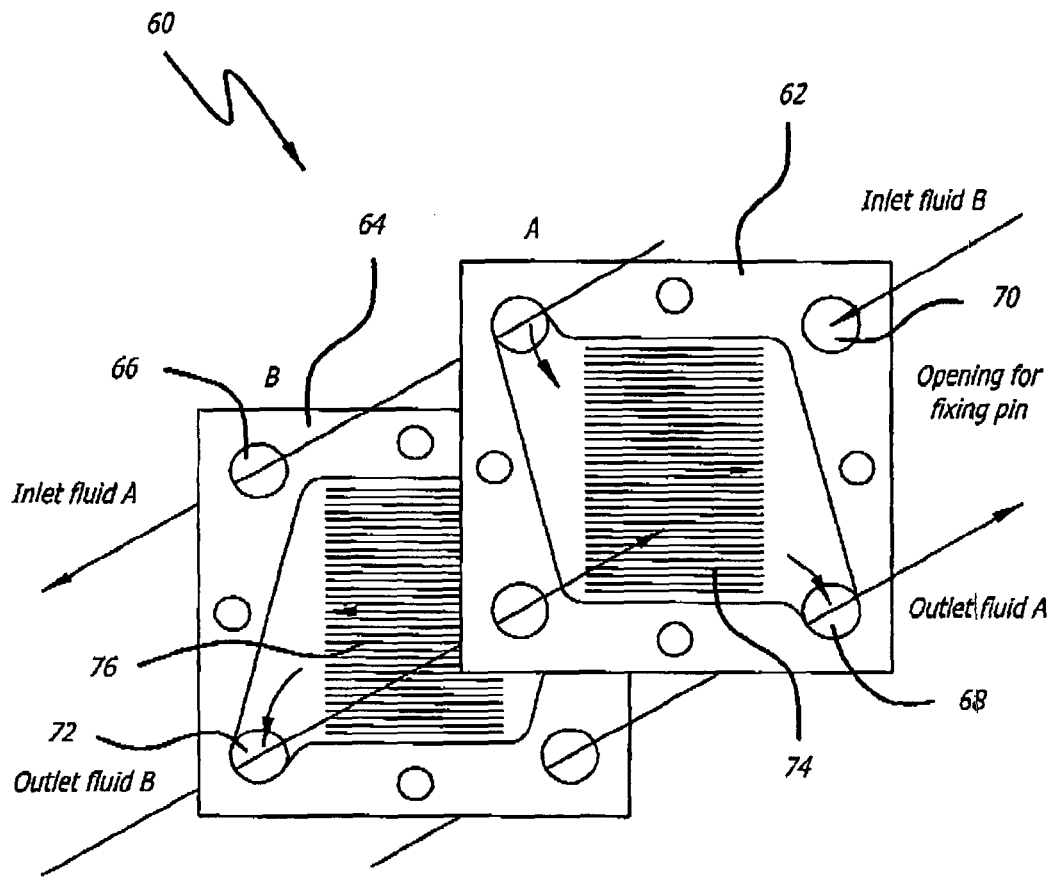
FIG. 5 is an exploded isometric view of heat exchanger for use in one embodiment of the hydrogen reactor in accordance with the present invention.

In other embodiments, the heat exchangers are stacked plate-type heat exchangers. FIG. 5 is an exploded isometric view of a stacked plate-type mesochannel heat exchanger 60 for use in the present invention. The heat exchanger includes a first plate 62 and a second plate 64 encased in a housing (not shown). Aligned through each plate are a first fluid, inlet, e.g., a fuel inlet or an oxygen inlet, 66, a first fluid outlet 68, a second fluid inlet, e.g., a combustion by-product or a reaction product inlet, 70, and a second fluid outlet 72. The first fluid flows in through the first fluid inlet, than flows through a plurality of mesochannels 74 formed on the surface of the side of the first plate opposite the second plate, and then out through the first fluid outlet. The second fluid flows in through the second fluid inlet, then flows in direction opposite to the direction of flow of the first fluid, through a plurality of mesochannels 76 formed on the surface of the side of the second plate adjacent the first plate, and then out through the second fluid outlet through.

In one embodiment, such heat exchangers are produced from 25 micron stainless steel foils, which are bonded using electroplating. Ceramic heat exchangers of a similar design can also be employed. Such mesochannel heat exchangers have up to 97% efficiency, while at the same time being relatively light-weight. The pressure drop is extremely low—approximately 2" of water column.

In the embodiments where the heat exchanger is a stacked plate type heat exchanger, it is most preferable that the channels running between the plates have meso scale dimensions. Alternately, in a manner similar to the use of porous metal substrates in the reaction chamber and combustion chamber, mesochannel architecture in the heat exchangers can also be realized by incorporating porous metal foam or ceramic substrates with flow dimensions in the mesoscale range, with the difference that instead of machining channels into the plates, thin substrates can be sandwiched between the plates to provide mesochannel flow dimensions for fluid flow. While not specifically shown, both heat exchangers are insulated, so that little thermal energy is lost.

In those embodiments, where expediency in switching from ammonia to hydrocarbon fuels (and vice versa) is desired, the fuel tank 14 and the heat exchangers 28 and 30 are fabricated so that they are compatible with both ammonia and hydrocarbon fuels. In alternative embodiments, where it is desired to minimize the cost of the components, different fuel tanks and heat exchangers are used for different fuels. For example, not all seal materials are compatible with both ammonia and hydrocarbons. Some, generally more expensive seal materials are compatible with both. Furthermore, since ammonia and the water produced by combustion of ammonia form a corrosive mixture, corrosion resistant materials should be used, instead of stainless steel. Furthermore, it is preferable for such components to be able to be reused. That is, some materials may be chemically compatible with the fuel for only a short period of time. The hydrogen generator preferably is a reusable system, and thus the fuel supply and the fuel heat exchanger are preferably adapted to be used with the fuel for extended cycles. Therefore, rather than employing expensive materials for all such components, it may be beneficial to fabricate different heat exchangers and different fuel supplies specifically adapted to be compatible with a selected fuel (ammonia or hydrocarbon).

Turning now to the operation of the hydrogen generator 10, the system has both start up and steady state operational modes. The start up mode is the period in which fuel is burned to bring the reactor 12, and more specifically, the reaction catalyst, up to the required reaction temperature. During this start up period, little or no hydrogen is generated. The steady state mode of operation represents the time after the reactor has reached operating temperature, and the fuel is being primarily converted to hydrogen. In preferred embodiments, during the steady state mode, thermal energy is generated by combusting the by-products that are separated from the hydrogen using the hydrogen membrane. The by-products, or tail gas, are combined with air and burned, to extract the maximum thermal energy from the fuel.

Figure 6:
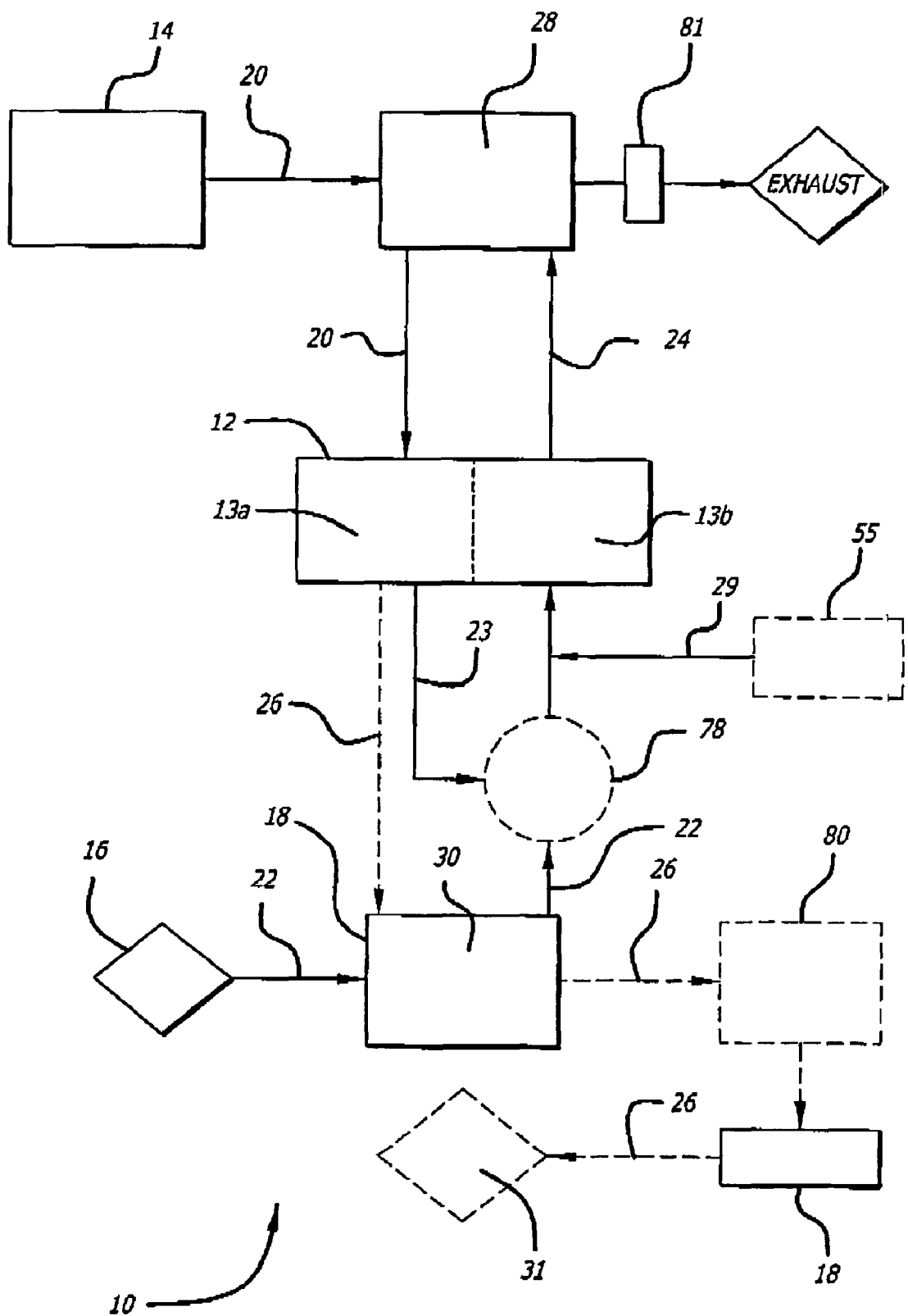
FIG. 6 is a block diagram corresponding to the hydrogen membrane reactor of FIG. 1, showing the system during a start up sequence.

FIG. 6 shows fluid flows for the hydrogen generator 10 in the start up phase according to one embodiment. Referring specifically to an embodiment where liquefied ammonia is the fuel, liquefied ammonia exits fuel tank 14 and flows through fuel supply line 20 into fuel heat exchanger 28. At start up, the fuel heat exchanger is cold, so no preheating of the ammonia occurs. However, the liquefied ammonia substantially volatilizes at room temperature without preheating, and so ammonia vapor flows through the fuel supply line into the reaction chamber 13a of the hydrogen membrane reactor 12. Because the reactor is cold (room or ambient temperature verses a preferred operating temperature of 650° C.) no disassociation occurs, and the "tail gas" exiting the reaction chamber through the tail gas supply line 23 is ammonia. That ammonia is then fed into the combustion chamber 13b, along with ambient air transported through the oxygen supply line 22 from the oxygen supply 16. At this time, the oxygen heat exchanger 30 is also at ambient temperature, so that no preheating of air introduced into the combustion chamber occurs.

Alternately, a supplemental fuel such as hydrogen can be used to light-off the combustion catalyst. In this alternative embodiment the hydrogen is fed to the combustion chamber 13b from the supplemental fuel supply 55 through the supplemental fuel supply line 29 in fluid communication with the oxygen supply line 22. In particular during start-up hydrogen stored in hydrides for example can be introduced into the air supply line in a manner to prevent undesirable auto-ignition prior to entry into the combustion chamber.

The use of hydrogen circumvents the need for using a toxic fuel such as ammonia during start-up, as slippage of ammonia past the combustion chamber needs to be handled carefully. In another embodiment, when ammonia is used as the fuel to the reaction chamber, a second fuel such as propane can be used as the fuel to the combustion chamber once light-off has been effected using hydrogen as a supplemental fuel.

Additionally where ammonia is utilized as a fuel supply, flowing the combustion product gases through an ammonia adsorbent supply during start-up can also be accomplished. This prevents ammonia slippage from the combustion chamber during the start-up sequence.

In the combustion chamber 13b of hydrogen membrane reactor 12, the ammonia and air, in the presence of the combustion catalyst, are ignited. As the reactor initially heats up, combustion by products exiting the reactor through combustion by-product line 24 cause the fuel heat exchanger 28 to begin to heat up as well. The heat, in turn, causes the ammonia traveling through fuel supply line 20 to be preheated, further adding thermal energy to the reactor. The start up phase continues until the catalyst is heated up to its own light off temperature. At that point, the ammonia disassociation reaction is enabled, and the system enters a steady state.

Figure 7:
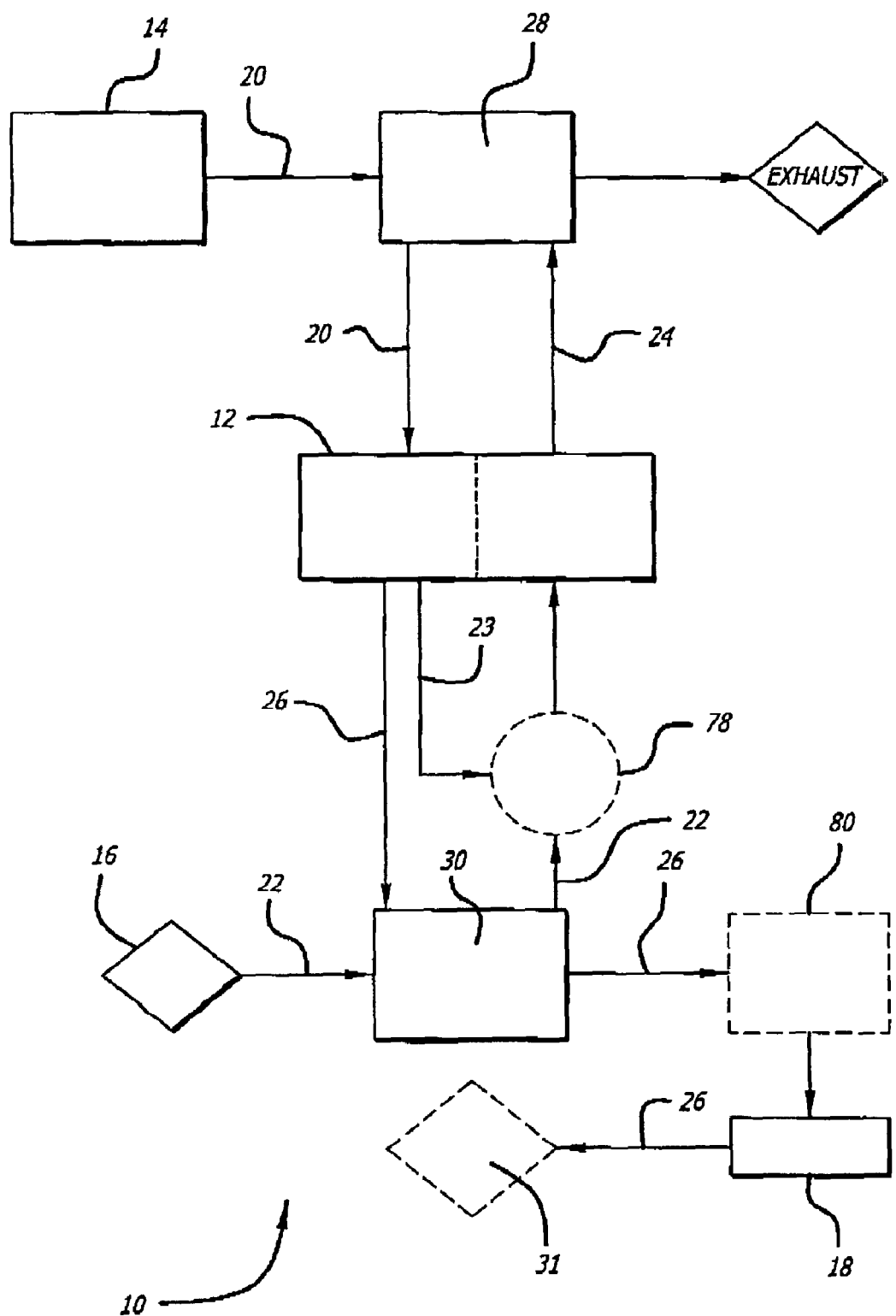
FIG. 7 is a block diagram corresponding to the hydrogen membrane reactor of FIG. 1, showing the system during a steady state sequence.

FIG. 7 shows fluid flows for the hydrogen generator 10 in the steady state. In the steady state, as illustrated in FIG. 7, ammonia entering the reaction zone of the reaction chamber 13a through fuel supply line 20 disassociates into hydrogen and nitrogen as illustrated in the reaction (1) reported in section [0014] above.

The majority of the hydrogen passes through the hydrogen membrane (not shown) and travels through the hydrogen exhaust channels (not separately shown) out of the membrane reactor through reaction product line 26. The hydrogen membrane allows hydrogen to diffuse across the membrane, eliminating the need for a further separation step to obtain a relatively pure hydrogen stream. Besides separating the desired hydrogen stream from other reaction products, the hydrogen membrane favorably affects the kinetics of the hydrogen generation reaction. By continually removing hydrogen from the reaction zone, the membrane causes an imbalance in the reaction kinetics that drives the conversion of more fuel into hydrogen in response to this imbalance. This conversion further increases the efficiency of the process, as without such a driving force, additional thermal energy would be required to drive the hydrogen generation reaction.

The hot hydrogen passes through the hydrogen membrane, into the hydrogen exhaust zone and then out of the hydrogen membrane reactor 12 through the reaction product line 26. The hot hydrogen enters oxygen heat exchanger 30 and is cooled by the ambient air transported through the oxygen supply line 22, which in turn is preheated before entering hydrogen the hydrogen membrane reactor. The tail gas now includes primarily nitrogen with traces of unreacted ammonia and hydrogen that did not pass through the hydrogen membrane. The tail gas has some fuel value (due to the traces of ammonia and hydrogen) and enters the combustion chamber of hydrogen membrane reactor, where combustion of the tail gas provides sufficient thermal energy to maintain the required thermal conditions in hydrogen membrane reactor for self-sustaining disassociation and combustion reactions to occur, so long as the ammonia from ammonia storage tank 14 is provided.

Figure 8A:
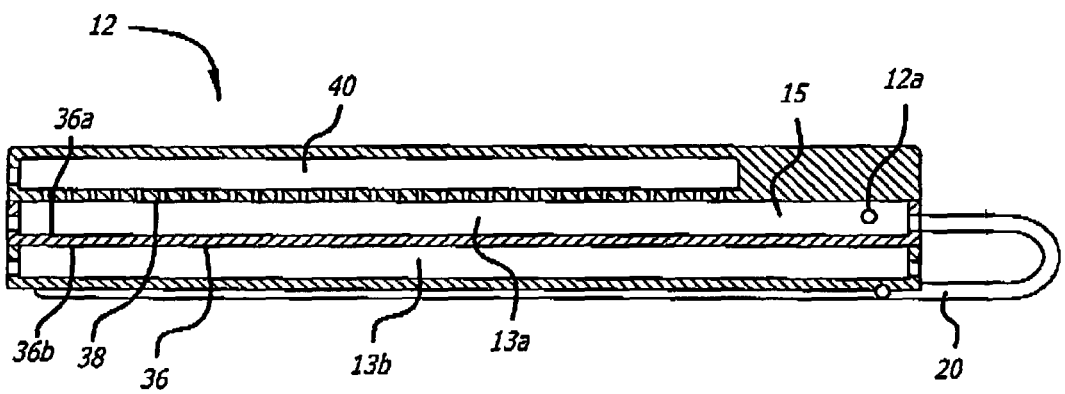
FIG. 8a is a sectional view of a hydrogen membrane reactor according to the invention.
Figure 8:
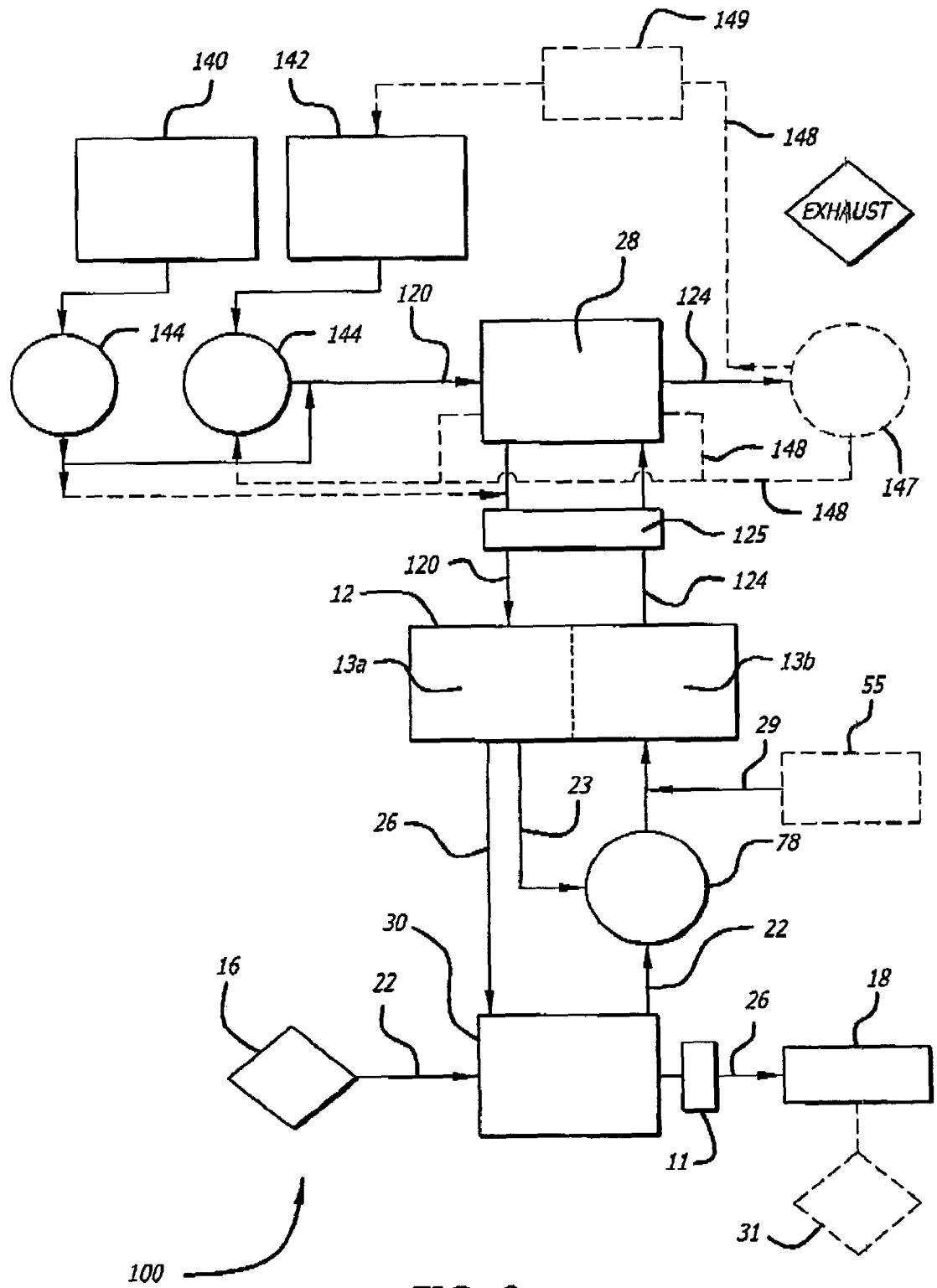
FIG. 8 is a block diagram illustrating the primary components of an alternative hydrogen generator in accordance with the present invention.

FIG. 8 illustrates fluid flows for an alternative hydrogen generator 100 based on a hydrocarbon steam reformation reaction. In this embodiment, the hydrogen produced is used to power a fuel cell (or for other purposes as described above) while the CO and other reactor tail gases such as methane are combusted to provide thermal energy to sustain the steam reforming reaction.

The hydrogen generator 100 shares many features with the hydrogen generator 10 and similar elements are identified with similar numbers. The difference is that hydrogen generator 100 also incorporates a water supply system to provide steam for the steam reforming reaction. The feed supply system includes a hydrocarbon fuel tank 140, a water storage tank 142, and hydrocarbon/water pumps 144. If a pressurized hydrocarbon (such as natural gas or propane) is employed as the fuel, the pressure alone would be enough to drive the fuel through the hydrogen generator. However, if a liquid hydrocarbon, such as JP-8 is employed, the hydrocarbon pump will be required. Regardless, the pump 144 provides a motive force to drive water from the water storage tank though fluid supply line 120 into the hydrogen membrane reactor 12. A fuel heat exchanger 28 operably connected to the fuel supply line and a combustion by-product line 124 is included to transform the water into steam and to preheat the hydrocarbon fuel.

In another embodiment, the liquid hydrocarbon fuel and liquid water that are fed to the reaction chamber 13a are metered using separate liquid pumps 144. This configuration is particularly useful in the event that the hydrocarbon fuel and water form an immiscible mixture. When fuel and water form miscible mixtures such as alcohol-water (ethanol, methanol etc), a single pump is used to meter the fuel-water mixture into the reaction chamber.

During steam reformation of hydrocarbon fuels, the formation of carbon deposits in the reaction chamber or on other hot surfaces is undesirable. Carbon formation can be mitigated to some extent by employing suitable methods for contacting the fuel and water. In one embodiment, it is desirable to vaporize the water to steam and pre-heat the steam prior to contacting with the hydrocarbon fuel that is fed to the reaction chamber. The steam/water vapor is typically pre-heated to a temperature in the range of the boiling point of liquid hydrocarbon fuel comprising the hydrocarbon supply and is contacted with hydrocarbon fuel from the hydrocarbon supply prior to entering the pre-treatment chamber chamber (125). Vaporization and pre-heating of water can be effected by exchanging heat with the reactor tail gases. Alternately, the water feed line can be routed close proximity to the combustion chamber to exchange heat with the combustion chamber. In one embodiment, the pre-heated water vapor and hydrocarbon fuel flow are contacted while flowing in an orthogonal manner to each other.

Additionally, it would be beneficial to contact the pre-heated steam and the hydrocarbon fuel in a pre-treatment chamber chamber 125 that contains a suitable catalyst to convert a portion of the hydrocarbon fuel to hydrogen containing gases prior to entry into the membrane reformer. The pre-treatment chamber is employed to improve utilization of the membrane surface area for hydrogen separation. The pre-treatment chamber does not contain the membrane, and is typically situated in a region where the temperature is typically in the 400 to 600° C. range. The pre-treatment chamber 125 could be located near the fuel side exit of the fuel heat exchanger 28 or in a separate chamber that is in fluid communication and in a heat exchange relation with the combustion chamber.

Alternately, in some embodiments, the membrane need not be placed where the fuel and pre-heated water first enter the reaction chamber of the membrane reactor 12. In such embodiments, the hydrogen membrane reactor includes a non-membrane leader portion of a suitable length to insure that the product gas inside the reactor first contacts the membrane only after the hydrocarbon fuel has been pre-reformed to generate some hydrogen.

Hydrogen generator 100 includes a hydrogen membrane reactor 12 having two separate chambers, a reaction chamber 13a in a heat exchange relationship with a combustion chamber 13b. In a preferred embodiment, the reaction chambers each incorporate mesoscale channels that are incorporated into the components of the reaction chambers or in porous catalyst substrates to enhance the reaction efficiencies.

The reaction chamber incorporates a steam reforming catalyst, while the combustion chamber incorporates a catalyst to facilitate the combustion of the selected hydrocarbon fuel. Catalysts for steam reforming of hydrocarbons and combustion of hydrocarbons are readily available from a variety of sources. For example, Sud Chemie, Inc (Louisville, Ky.) and the catalyst division of Johnson Matthey, in Wayne, Pa., provides suitable catalysts. The reaction catalysts have characteristic "light-off" temperatures, as well as a characteristic optimal temperature. These temperature parameters affect a specific reactor design by defining minimum and optimum reactor temperatures. In a preferred embodiment, the desired reactor temperature will be less than 650° C., so that conventional metals (rather than high temperature refractory metals) can be used to fabricate the hydrogen membrane reactor. In one embodiment, the catalysts are incorporated as packed beds, while in another embodiment the catalysts are deposited on surfaces of the reaction chamber and the combustion chamber.

In some embodiments, the hydrogen generator 100 includes a water recovery system, to reduce the amount of water required. This feature is particularly advantageous if a small and compact system is required. Such a water recovery system is in fluid communication with the pump 144, and includes a water pump 147, a recovered water return line 148 that is in fluid communication with the fuel heat exchanger 28, such that the water fraction from the cooled combustion products exiting the fuel heat exchanger is recycled through the recovered water line 148, while other combustion products are simply exhausted. A recovered water reservoir 149 can also be included in the system in communication with the recovered water line 148.

In some embodiment, the hydrogen generator 100 includes a hydrogen supply 55, for transporting hydrogen to the combustion chamber 13b, through a hydrogen supply line 29. In those embodiments, the hydrogen can be used as a supplemental fuel in a start-up sequence described in FIG. 9 below.

In some embodiments, the hydrogen generator 100 includes a methanator 11 located on the reaction product line 26 to eliminate traces of CO possibly present in the reaction product and convert them in $CH_4$.

During steam reformation of hydrocarbons, if defects in the membrane were to arise, leakage of entities such as CO, $CO_2$ and $CH_4$ into the hydrogen product may arise. While the presence of these components in trace amounts would not be detrimental to certain end uses, the presence of CO at levels greater than 50 ppm could render the hydrogen product unsuitable for PEM fuel cell use. Trace levels of CO contaminant can be effectively destroyed using processes such as methanation or preferential oxidation. Methanation is a preferred route since the residual CO is reacted with the hydrogen (major component) in the product to yield benign $CH_4$. In preferential oxidation, a source of air is bled into the hydrogen product, which could lead to run-away reactions. Methanation is typically effected at temperatures less than 200° C. over catalysts such as T-4308 type as supplied by Süd Chemie, Inc (Louisville, Ky.). The small catalyst bed or catalyst coated substrate can be located in a suitable position such as in the heat exchanger that is used to cool the product hydrogen or in any other position where a temperature of about 200° C. can be realized.

FIG. 8a shows a sectional view of a hydrogen membrane reactor 12 in an embodiment wherein a non-membrane leader portion is included. A portion of the reaction chamber 13b situated close to the entry port of the reaction chamber constitutes the pre-reforming chamber 15. This pre-reforming portion of the reaction chamber is differentiated from the rest of the reaction chamber by the absence of the membrane 38. In other words, the membrane does not extend into the pre-reforming chamber. During the steam reformation of hydrocarbons for example, water is vaporized in the water supply line 20 that is in contact with the external surface of the combustion chamber 13b. Water may be further heated beyond the normal boiling point and enters the pre-treatment chamber chamber 15. Fuel enters the pre-treatment chamber chamber through the port 12a. In the pre-treatment chamber chamber, the fuel is partially converted to a gaseous mixture containing hydrogen and this gaseous mixture flows into the reaction chamber 13b that contains the membrane 38. This insures that the membrane surface is exposed to a reducing mixture (due to the presence of hydrogen) that would prevent the deterioration of the membrane by oxidation. Hydrogen is separated through the membrane and into the exhaust zone 40.

Figure 9:
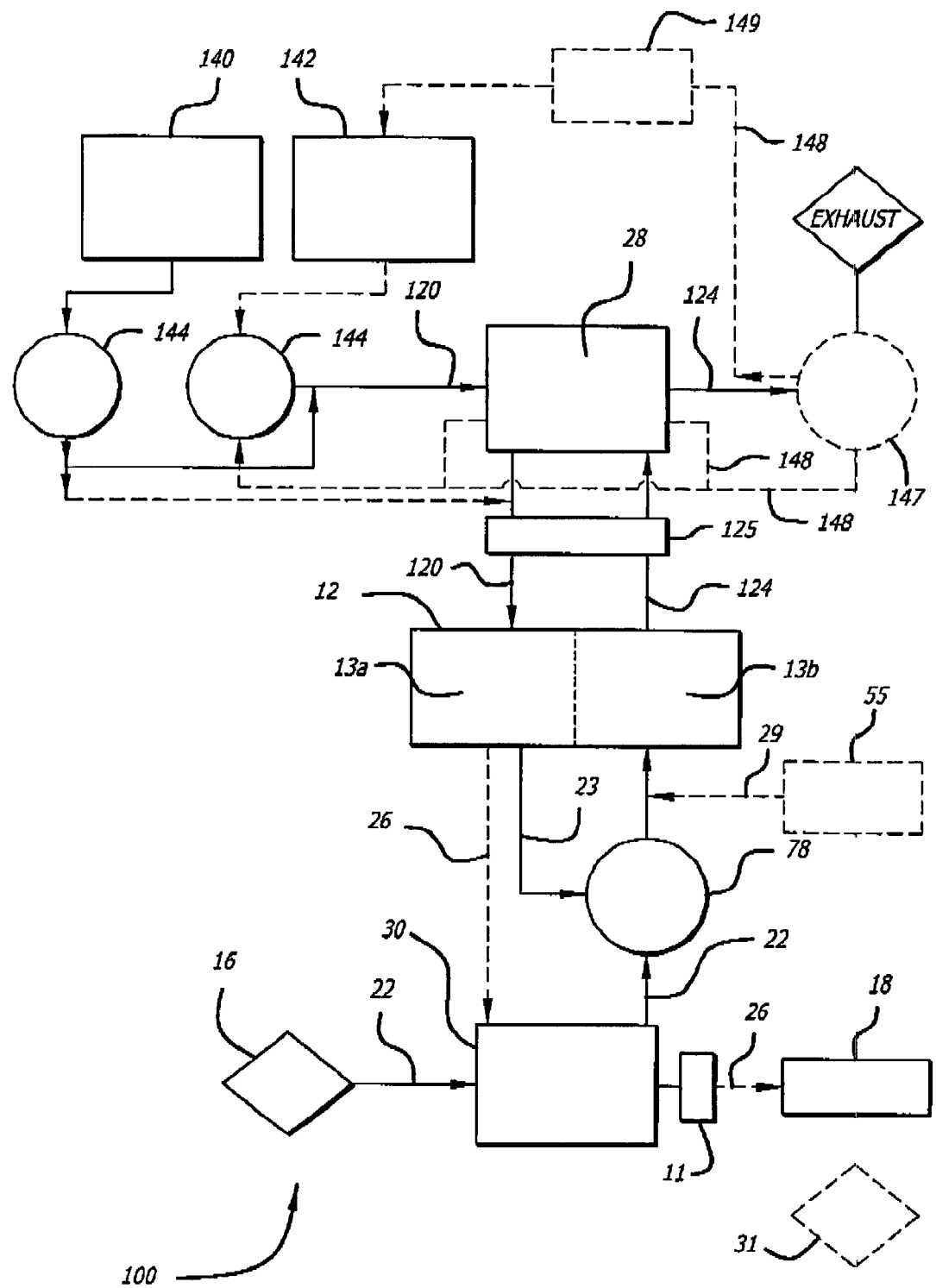
FIG. 9 is a block diagram corresponding to the hydrogen membrane reactor of FIG. 8, showing the system during a start up sequence.

FIG. 9 shows fluid flows for the hydrogen generator 100 in a start up phase. The hydrocarbon fuel from hydrocarbon storage tank 140 is transported through the fuel supply line 120 (using the fuel pump 144 if a non-pressurized fuel is employed) into the fuel heat exchanger 28. Because the fuel heat exchanger is cold at startup, steam generation and hydrocarbon preheating cannot occur. Also, because hydrogen membrane reactor 12 is cold (ambient temperature versus 650° C.) no steam can be generated for steam reformation via heat exchange.

The hydrocarbon first enters the reaction chamber. At start up, no steam reformation can occur, and the "tail gas" exiting the reaction chamber though tail gas supply line 23 will be pure hydrocarbon. That hydrocarbon is then fed through the tail gas supply line into the combustion chamber, along with ambient air transported through oxygen supply line 22 from oxygen supply 16. At this time, the oxygen heat exchanger 30 is also at ambient temperature, so that preheating of the air introduced into the hydrogen membrane reactor 12 does not yet occur.

In the combustion reaction chamber of hydrogen membrane reactor 12, the hydrocarbon and air, in the presence of the combustion catalyst, are ignited. As the reactor initially heats up, combustion products exiting the reactor cause the fuel heat exchanger 28 to begin to heat up as well, which causes the hydrocarbon fuel from storage tank 140 to be preheated, further adding thermal energy to the reactor. The start up phase continues until the reaction catalyst is heated to its light off temperature. At that point, water is released from storage tank 142. If pump 144 is not yet on, it is now energized. The fuel heat exchanger 28, now hot due to the heat of the combustion products exiting the combustion chamber, transforms the water to steam. The steam reformation reaction is now enabled, and the system enters a steady state.

In an alternate embodiment, room temperature light-off of the combustion catalyst is achieved using hydrogen that is stored in a hydrogen supply 55 and fed to the combustion chamber through a hydrogen supply line 29 in fluid communication with the oxygen supply line 22. When the combustion catalyst temperature reaches 200 C. -300° C., the hydrogen fuel is replaced with a hydrocarbon fuel that may be different from the fuel that is to be fed to the reaction chamber. Fuel to the combustion chamber (which may be tail gas, supplemental fuel such as hydrogen, a second fuel as shown in FIG. 1) is mixed with air in the air supply line 22 and transported into the combustion chamber. During start-up hydrogen stored in hydrides for example, is introduced into the air supply line in a manner to prevent undesirable auto-ignition prior to entry into the combustion chamber. The second fuel, for example propane, is metered in the same manner as hydrogen into the air supply line.

When the temperature of the catalyst in the reaction chamber reaches between 550 to 650° C., the hydrogen-producing fuel is contacted with water vapor that is preheated to about 300° C. to about 550° C. or close to the normal boiling point of the hydrogen producing fuel before a pre-treatment chamber or pre-reformation chamber 125 to produce hydrogen containing product gases. The flow of external fuels to the combustion chamber can be reduced or terminated once reactor tail gases are available for combustion.

The pre-treatment chamber chamber 125 can be situated external to the reaction chamber or can constitute a portion of reaction chamber that is situated close to the feed inlet and in addition, does not contain a membrane.

The resultant pre-reformed gas mixture flows through the reaction zone to produce hydrogen and reaction tail gases. Hydrogen is separated therefrom while produced through the hydrogen separation membrane.

Water present in the reaction tail gases is condensed in the heat exchanger 28 by cooling and pressure reduction, and recycling water to a water supply 142 or 149 or to the water line 148. In another embodiment, the water present in the combustion chamber product gases is condensed by heat exchange with the incoming air in the heat exchanger 30 and routing the resultant gas to the combustion chamber and recycling the water to the water supply. The dry and cooled combustion chamber product gases are vented to the atmosphere.

A methanator 11 can also be included in the hydrogen generator 100, and located in the reaction product line 26 to eliminate CO traces from the reaction product.

Figure 10:
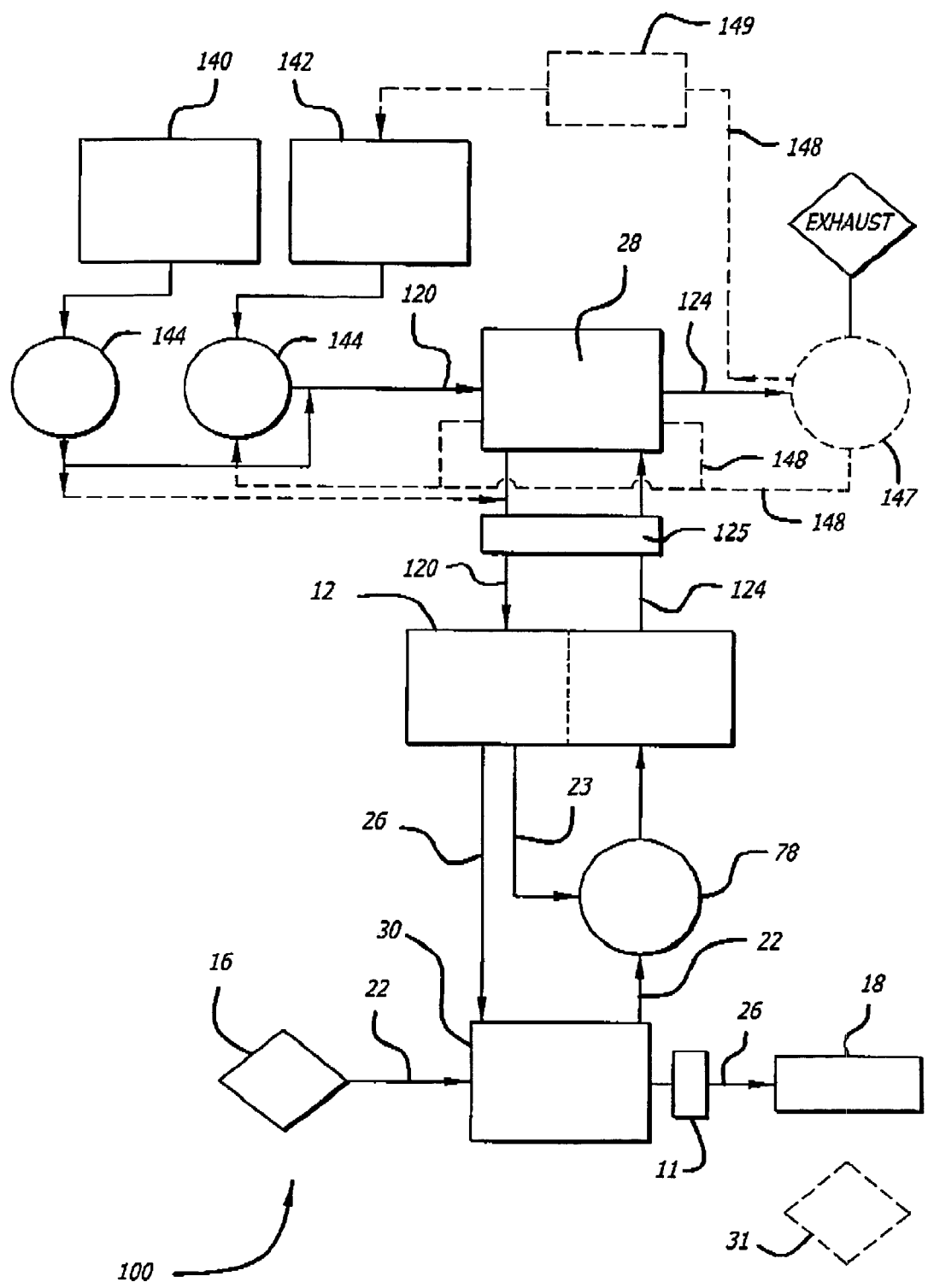
FIG. 10 is a block diagram corresponding to the hydrogen membrane reactor of FIG. 8, showing the system during a steady state sequence.

FIG. 10 shows fluid flows for the hydrogen generator 100 in the steady state. In the steady state, as illustrated in FIG. 10, steam and hydrocarbons entering the reaction are reformed into hydrogen, carbon monoxide, carbon dioxide and methane. The majority of the hydrogen exits the reaction chamber 13a by passing through the hydrogen membrane (not shown), into the hydrogen exhaust zone (not shown), and then out of the hydrogen membrane reactor through the reaction product line 26. This hot hydrogen enters oxygen heat exchanger 30 and is cooled by ambient air from the oxygen supply 16, which is routed into the heat exchanger 30 through the oxygen supply line 22, and is in turn is preheated before entering the combustion chamber 13b. The hot hydrogen in the reaction product line 26 can also be cooled by exchanging heat with the incoming cold feed. The tail gas routed in the tail gas supply line 23 now includes primarily carbon monoxide with unreformed hydrocarbons and carbondioxide, and hydrogen that did not pass through the hydrogen membrane and has significant fuel value. The tail gas enters the combustion chamber 13b, where combustion of the tail gas provides sufficient thermal energy to maintain the required thermal conditions in the hydrogen membrane reactor for self sustaining steam reformation and combustion reactions to occur, as long as hydrocarbon fuel and steam are provided. At this point, the combustion of reactor tail gases can substantially reduce or totally eliminate the need for supplying a supplementary fuel from the hydrogen supply 55 directly to the combustion chamber 13b.

In one embodiment, when hydrogen is produced by the steam reformation of hydrocarbons, excess water (above the stoichiometric requirement) is fed into the reaction chamber 13a to mitigate coke formation. Subsequently, the tail gases exiting reaction chamber 13a would contain un-reacted water which can constitute as much as 40 to 50% by volume of the tail gases, depending on the fuel that is used. In such cases, it may be beneficial to remove the water from the tail gases before routing the tail gases into the combustion chamber 13b, since large amounts of water generally quenches the combustion reaction. Removal of water from the reactor tail gases can be accomplished by exchanging heat with the incoming water feed (see for example the heat exchanger shown in FIG. 4A), by which heat from the hot tail gases is used to vaporize the incoming water feed and thereby condensing and cooling the water in the tail gases. The condensed water is collected and can be recycled to the water source 149 or 142 through the supply line 148.

Since the reactor tail gases exit the reactor under pressure, a pressure reduction component such as a back pressure regulator needs to be employed either upstream or downstream of the condenser.

Because the vaporization process is an endothermic process (energy is consumed in the process), the liquid, or liquefied gaseous, fuel exiting the fuel tank 14 advantageously vaporizes in the fuel heat exchanger 28. For example, in returning to the gaseous state, liquefied ammonia (or other liquid fuel) absorbs substantial amounts of heat from its surroundings (i.e. one gram of ammonia absorbs 327 calories of heat). Therefore, when the vaporization occurs in heat exchanger 28, it obviates the need for additional fuel to be consumed in the reactor to generate the thermal energy that would otherwise have been necessary to drive the vaporization process. Thus, what would otherwise be waste heat is employed to vaporize the liquefied ammonia (or other fuel).

Now water is produced during the combustion process and the gases leaving the combustion chamber are cooled by exchanging heat with the incoming air to the combustion chamber 13b. The condensed water from the combustion exhaust gases is also recycled to the water source constituted by the water tank 142. Additionally, in services where the availability of water is deemed to be a logistic problems (example, remote power applications, portable applications, military applications), the excess fuel can be intentionally combusted in the combustion chamber to generate water to be used as feed to the reaction chamber to generate water to be used as a feed to the reaction chamber, which eliminates or drastically reduces the need to have continuous access to a water source.

For particular applications, exemplary hydrogen generators made in accordance with the present disclosure provide methods for using excess fuel for intentional combustion in the combustion chamber to generate water to be used as a feed to the reaction chamber. This embodiment provides a hydrogen generator that is self-sufficient, regarding water supply and can be a net water generator. In such an embodiment, excess heat generated as a result of water generation can be utilized or dumped to the environment. In such a configuration/use, the thermal efficiency is sacrificed to generate water for use as a feed to the reaction chamber or as a source of potable water.

Figure 11:
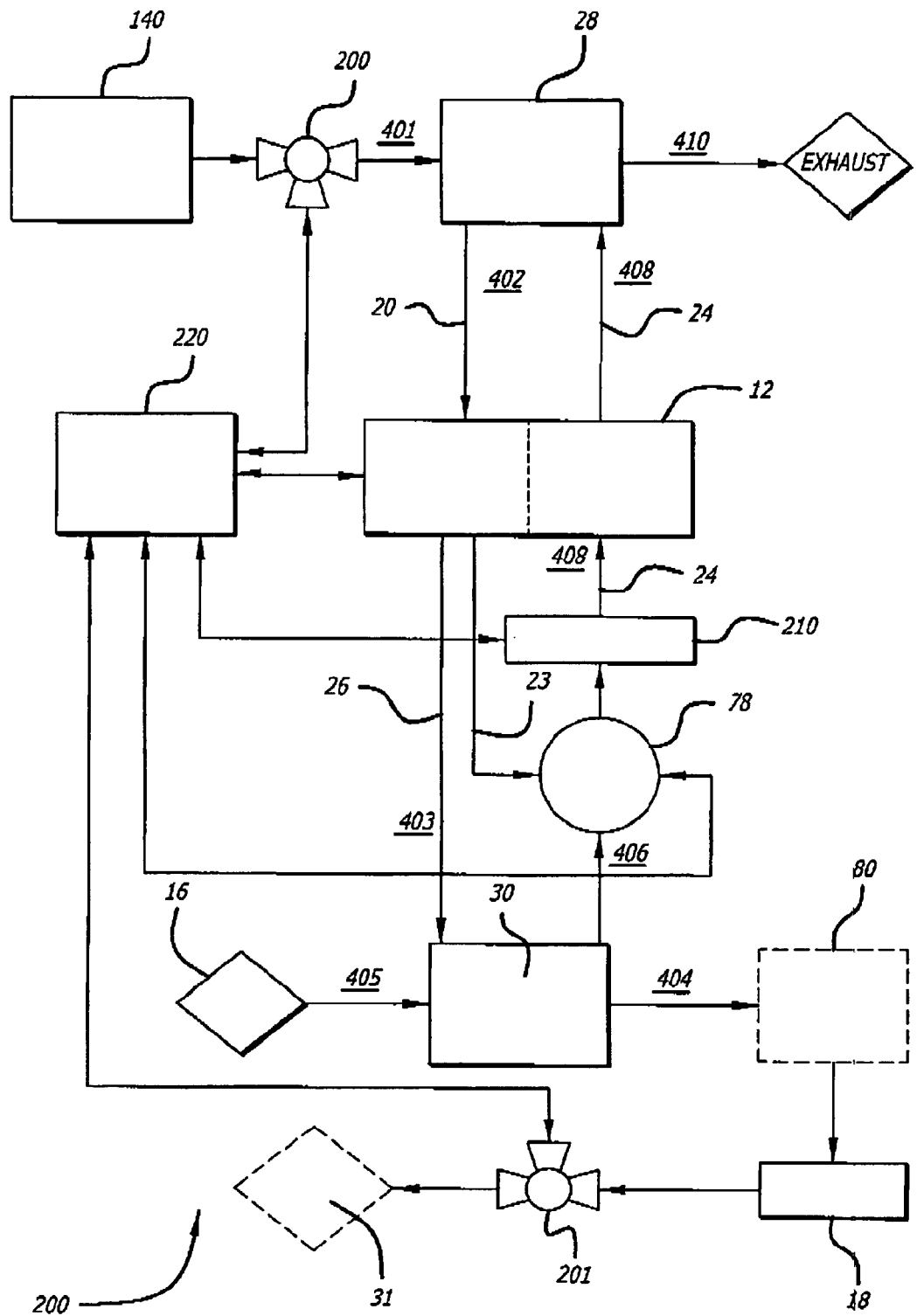
FIG. 11 is a block diagram illustrating the primary components of a second alternative hydrogen generator in accordance with the present invention.

FIG. 11 illustrates an ammonia-decomposition-based hydrogen generator 200 designed to produce 82 grams of hydrogen at a maximum production rate of 300 sccm, and a minimum production rate of 30 sccm.

The hydrogen generating system of FIG. 11 includes real-time, automated, and low power process control elements, including gas sensor technology, to provide an automated system that requires minimal user interaction. Miniature real-time gas sensors such as oxygen sensor 210 and miniature flow control valves, such as pressure regulatory valve 200 and valve 201, can be incorporated into compact systems. Preferably, a programmable microprocessor, such as μ p-based control or computer 220 is used to digitize sensor inputs and actuate flow control components. To minimize power consumption, such process control elements require low power. Lightweight components for pressure and temperature measurements are commercially available. Preferably, the only composition sensor required by the process control system is an oxygen sensor, which is commercially readily available, having been developed for the automotive industry.

It is an advantage of the hydrogen generator if are no rotating parts, such as fans, blowers or pumps. The absence of such components reduces noise, reduces parasitic power consumption, and increases reliability.

In some embodiments, the hydrogen generator is designed to operate in a submerged environment for short periods, with an energy density of 2000 watt hours/kg. The performance requirements for such embodiments are based on a three-day period, requiring a total energy of approximately 1500 watt hours. The total hydrogen generator weight is less than 1 kg (about 720 g). Further, the hydrogen generator provides a 20 watt average power output level. Peak sustainable output is about 30 watts. To meet these energy requirements, the hydrogen generator is designed to produce a total of approximately 75 grams of hydrogen.

Table I shows the weight of fuel required by such designs, given the conversion efficiency provided.

TABLE I

Fuel Weight Requirements for Three-Day Period

| Fuel | Est. Efficiency of Hydrogen Generator | Mass of Fuel |
|---|---|---|
| Ammonia | 95% | 499 |
| JP-8 | 80% | 245 |

Based on a complete analysis, accounting for chemical equilibrium, mass balances, energy balances and assumed heat exchanger efficiencies of 95%, mass flow rates are indicated that correspond to a hydrogen production rate of 235 sccm. This hydrogen generation rate is required to produce 20 watts of electric power, the desired average output for this system.

Table II reports the mass flow rates, compositions, temperatures, and pressures of various steps of the method for producing hydrogen carried out in the hydrogen generator of FIG. 11 where the generator is on a steady state. Those steps are identified in FIG. 11 with numerals from (401) to (410) located proximate to the portion of the hydrogen generator of FIG. 11 wherein they occur.

TABLE II

Process Parameters at Steady State and Full Hydrogen Output

| Process step | Pressure (psia) | Temperature (C.) | Composition (mole fraction) | Mass Flow (g/h) |
|---|---|---|---|---|
| (401) | 60 | 25 | $NH_3 = 1.0$ | 7.2 |
| (402) | 60 | 577 | $NH_3 = 1.0$ | 7.2 |
| (403) | 15 | 600 | $H_2 = 1.0$ | 1.09 |
| (404) | 15 | 66 | $H_2 = 1.0$ | 1.09 |
| (405) | 14.7 | 25 | $N_2 = 0.79/O_2 = 0.21$ | 6.2 |
| (406) | 14.7 | 571 | $N_2 = 0.79/O_2 = 0.21$ | 6.2 |
| (407) | 60 | 600 | $N_2 = 0.69/H_2 = 0.30/NH_3 < 0.01$ | 6.2 |
| (408) | 15 | 594 | $N_2 = 0.74/O_2 = 0.1/H_2 = 0.16$ | 12.4 |
| (409) | 15 | 600 | $N_2 = 0.8/O_2 = 0.02/H_2O = 0.18$ | 13.1 |
| (410) | 14.7 | 350 | $N_2 = 0.8/O_2 = 0.02/H_2O = 0.18$ | 13.1 |

Table III reports the size and weight of the various components.

TABLE III

Size and Mass Estimates for Key Components

| Component | Size (cm³) | Mass (g) |
|---|---|---|
| Reactor | 2 × 2 × 8 = 32 | 40 |
| Ammonia thermal exchanger | 1 × 2 × 8 = 16 | 20 |
| Air thermal exchanger | 1 × 2 × 8 = 16 | 16 |
| Packaging, plumbing and controls | 40 | 50 |

Figure 12:
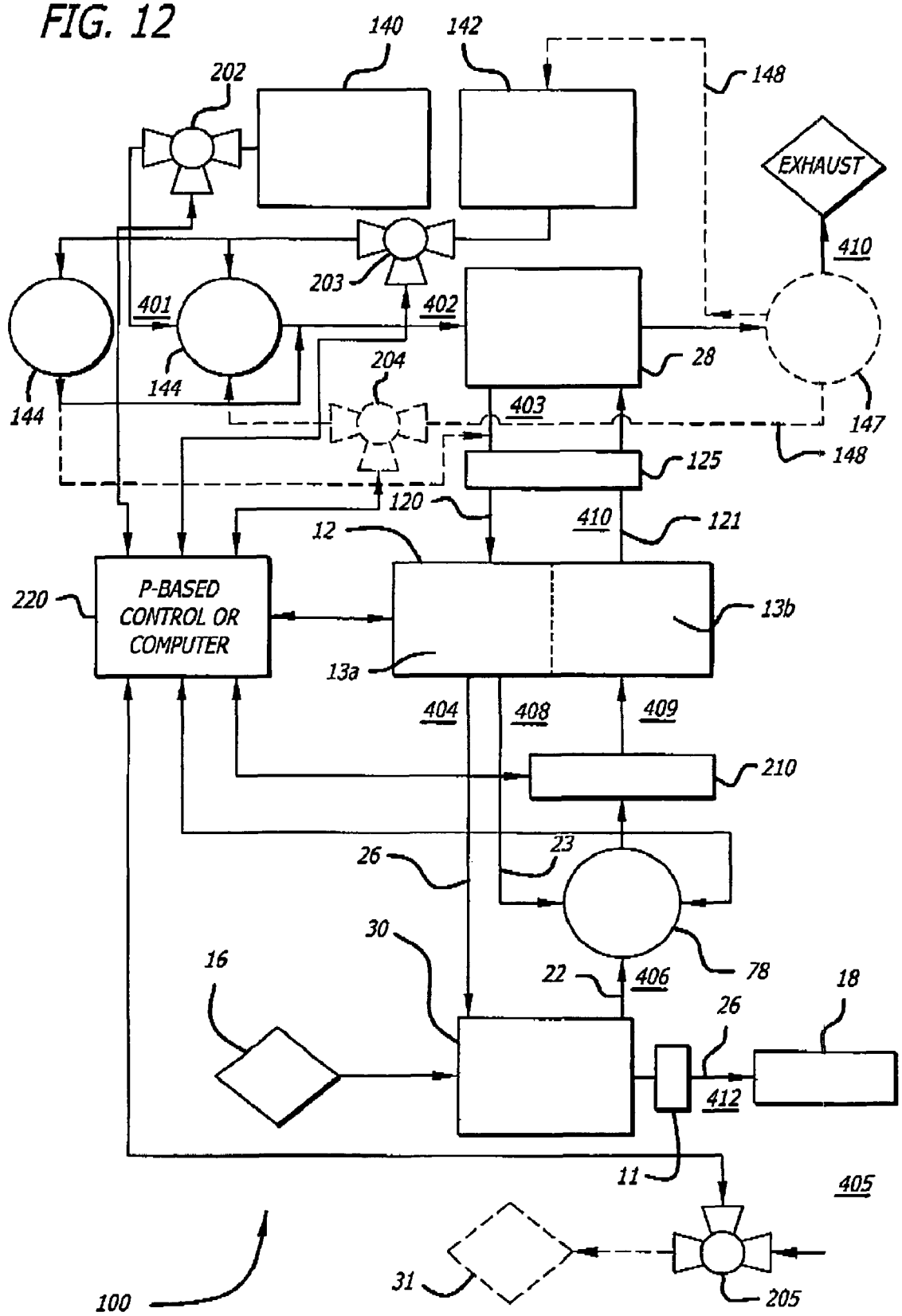
FIG. 12 is a block diagram illustrating the primary components of a third alternative hydrogen generator in accordance with the present invention.

FIG. 12 illustrates a hydrocarbon steam reformation-based hydrogen generator 300. The generator is designed to produce 80 grams of hydrogen at a maximum production rate of 200 sccm from a synthetic kerosene hydrocarbon fuel. The hydrogen generating system of FIG. 12 includes real-time, automated, and low power process control elements, including gas sensor technology, to provide an automated system that requires minimal user interaction. Miniature real-time gas sensors such as oxygen sensor 210 and miniature flow control valves 200 to 204, and in particular pressure regulatory valve 200 and valve 201, can be incorporated into compact systems. Preferably, a programmable microprocessor, such as µ p-based control or computer 220 is used to digitize sensor inputs and actuate flow control components. To minimize power consumption, such process control elements require low power.

Lightweight components for pressure and temperature measurements are commercially available. Preferably, the only composition sensor required by the process control system is an oxygen sensor, which is commercially readily available, having been developed for the automotive industry. It is an advantage of the hydrogen generator if are no rotating parts, such as fans, blowers or pumps are employed. The absence of such components reduces noise, reduces parasitic power consumption, and increases reliability.

In FIG. 12, the vaporized fuel/water mixture is pre-reformed to hydrogen containing gas mixture prior to being fed into the reaction chamber 13a. The heat for pre-reformation is supplied by the hot combustion byproduct gases. Hydrogen exiting the reaction chamber is cooled by exchanging heat with incoming air in heat exchanger 30 and is routed through a methanator 11 to destroy any impurities such as CO. Water from the cooled combustion byproduct gases is recovered and recycled. The dry combustion byproduct gases are vented out.

Based on a complete analysis, accounting for chemical equilibrium, mass balances, energy balances and assumed heat exchanger efficiencies of 96%, mass flow rates are indicated that correspond to a hydrogen production rate of 200 sccm.

Table IV reports the mass flow rates, compositions, temperatures and pressures of various steps of the method for producing hydrogen carried out in the hydrogen generator of FIG. 12 where the generator is on a steady state. Those steps are identified in FIG. 12 with numerals from (401) to (412) located proximate to the portion of the hydrogen generator of FIG. 12 wherein they occur.

An exemplary method for generating hydrogen in accordance with the present disclosure comprises the steps of flowing a supplemental fuel, such as hydrogen from a hydrogen supply and air into a combustion chamber of a hydrogen membrane reactor to achieve room temperature light-off by catalytic combustion. The combustion chamber is provided so as to be in fluid connection with and in heat exchange relationship with a reaction chamber, the reaction chamber having a reaction zone and containing a reaction catalyst. The reaction chamber is initially at a temperature less than the reaction catalyst's light-off temperature and the reaction zone is separated from a hydrogen exhaust zone by a hydrogen separation membrane.

Flowing hydrogen into the combustion chamber is replaced with a combustible fuel at approximately a time when the combustion catalyst's temperature is in the range of about 200-300° C. Combustion is continued until the temperature of the reaction catalyst reaches about 550 to 650° C.; at which time a hydrogen-producing fuel is contacted with water vapor that is preheated to about 300° C. to about 450° C. or close to the normal boiling point of the hydrogen producing fuel before a pre-treatment chamber or in a pre-treatment chamber to produce hydrogen containing product gases. The resultant pre-reformed gas mixture flows through the reaction zone to produce hydrogen and reaction tail gases. Hydrogen is separated therefrom while produced through the hydrogen separation membrane.

The separated hydrogen gas then flows through a methanator having a methanation catalyst to convert CO slippage to $CH_4$. Water present in the reaction tail gases is condensed by cooling and pressure reduction, and routing resultant gas to the combustion chamber and recycling water to a water supply. The flow of external fuel to the combustion chamber is reduced and water present in the combustion chamber product gases is condensed by heat exchange with the incoming air to the combustion chamber and recycling the water to the water supply. The now dry and cooled combustion chamber product gases are then vented to the atmosphere.

The hydrogen exiting the methanator can be conducted into a hydrogen reservoir. This hydrogen can be compressed and stored in metal hydride materials. Such compression is preferably effected utilizing hydrides and heat from the hydrogen generator. The resultant stored hydrogen can be utilized for the cold start-up.

Additionally, in particular embodiments hydrogen exiting the methanator can be conducted into a fuel cell.

TABLE IV

Process Parameters at Steady State with Hydrogen Output for 20 Watts Power

| Process Point | Pressure (psia) | Temperature (C.) | Composition (mole fraction) | Mass Flow (g/h) |
|---|---|---|---|---|
| (401) | 14.7 | 25 | HC = 1.0 | 3.33 |
| (402) | 60 | 25 | HC = .04/$H_2O$ = .96 | 11.9 |
| (403) | 60 | 600 | HC = .04/$H_2O$ = .96 | 11.9 |
| (404) | 15 | 600 | $H_2$ = 1.0 | 1.09 |
| (405) | 15 | 25 | $H_2$ = 1.0 | 1.09 |
| (406) | 14.7 | 580 | $N_2$ = 0.79/$O_2$ = 0.21 | 12.3 |
| (408) | 60 | 600 | $CO_2$ = .38/CO = .19/$H_2O$ = .19/$H_2$ = .24 | 10.8 |
| (409) | 15 | 580 | $CO_2$ = .19/CO = .09/$H_2O$ = .21/$H_2$ = .12/$N_2$ = .40 | 23.9 |
| (410) | 14.7 | 600 | $N_2$ = .80/$CO_2$ = .28/$H_2O$ = .32 | 24.9 |
| (411) | 14.7 | 70 | $N_2$ = .57/$CO_2$ = .40/$H_2O$ = .03 | 20.3 |
| (412) | 14.7 | 70 | $H_2O$ = 1.0 | 4.64 |

Table V reports the size and weight of the various components.

TABLE V

Size and Mass Estimates for Key Components

| Component | Size (cm³) | Mass (g) |
|---|---|---|
| Reactor | 2 × 4 × 8 = 64 | 60 |
| Fuel/water thermal exchanger | 1 × 4 × 8 = 32 | 30 |
| Air thermal exchanger | 1 × 4 × 8 = 32 | 30 |
| Packaging, plumbing and controls | 60 | 200 |

In still additional embodiments, catalysts are coated onto metal foam substrates containing channels like features.

In particular embodiments having hydrogen produced through a methanator, a temperature spike in the methanator, caused by increased amounts of CO and $CO_2$ in the hydrogen product due the formation of defects in the membrane or membrane failure, is used to shut-down the system in a safe manner and to isolate the hydrogen generator from the fuel cell.

In still other embodiments, an exemplary hydrogen generator utilizing pre-reformation utilizes a suitable catalyst incorporated in a pre-reformation chamber that constitutes a membrane-less portion located at an entrance of the membrane reformer.

Now hydrogen separation rates through the membrane is dependent on the hydrogen partial pressure ($P_1$) in the reaction chamber 13b and the hydrogen partial pressure in the exhaust zone 40 ($P_2$). Higher values for $P_1$ and/or lower values for $P_2$ are desirable for hydrogen separation through the membrane. $P_2$ can be decreased by feeding an inert sweep gas into the exhaust zone 40 or by withdrawing hydrogen through a suction device. In general an inert sweep gas would result in diluting the hydrogen gas that flows through the membrane an is not suitable for PEM fuel cell use. If steam is used as the sweep gas, condensation of the steam from the hydrogen-steam gas mixture results in a non-condensable hydrogen gas that can be routed to the PEM cell. When compactness is desired, the use of a suction device may be more suitable for improving hydrogen separation.

Examples of these devices include a miniature vacuum pump or a micro ejector. In the case of micro-ejector a portion of the steam that is generated for the steam reformer can be used to supply the driving force to operate the micro-ejector. Table VI reports the effect of using a vacuum pump to reduce $P_2$ during steam reformation of propane in a membrane reactor. The membrane reformer contained a 25 micron thick 75% Pd-25% Ag foil. At a steam to carbon (S/C ratio) of 2.7 and at a gas hourly space velocity (GHSV) SV of 1500 $h^{-1}$, a 52% increase in hydrogen flow rate was achieved by employing vacuum.

TABLE VI

Effect of reducing permeate side $H_2$ partial pressure during steam reforming of propane. 650 C., 5.7 bar.

| GHSV [$h^{-1}$] | S/C | $P_2$ [bar] | $H_2$ leaving exhaust zone [sccm] |
|---|---|---|---|
| 1,500 | 2.7 | 1 | 423 |
| 1,500 | 2.7 | 0.45 | 641 |

Although the present invention has been described in connection with the preferred form of practicing it, those of ordinary skill in the art will understand that many modifications can be made thereto without departing from the spirit of the present invention. Accordingly, it is not intended that the scope of the invention in any way be limited by the above description.

We claim:

1. A method for generating hydrogen in a hydrogen membrane reactor having a combustion chamber defined by a bottom plate and a separation plate and a reaction chamber defined by a top plate and the separation plate, the combustion chamber in a fluid connection with and a heat exchange relationship with the reaction chamber, the combustion chamber including a combustion catalyst, the reaction chamber including a separation membrane defining a reaction zone and an exhaust zone in the reaction chamber, the combustion chamber comprising a plurality of combustion channels defined by a first set of spaced apart fins extending from the separation plate to and in contact with the bottom plate, the reaction zone comprising a plurality of reaction channels defined by a second set of spaced apart fins extending from the separation plate to and in contact with the separation membrane, the reaction zone including a reaction catalyst, the reaction catalyst having a reaction catalyst light-off temperature, the combustion catalyst light off temperature being lower than the reaction catalyst light off temperature, the method comprising:

a. flowing stored hydrogen into the combustion chamber at a combustion catalyst light off temperature for the stored hydrogen, the combustion of the stored hydrogen generating first combustion product gases;

b. replacing the flowing stored hydrogen into the combustion chamber with a combustible fuel different from the stored hydrogen at approximately a time when the temperature of the combustion catalyst reaches a combustion catalyst light-off temperature for the combustible fuel and continuing combustion to enable the temperature of the reaction catalyst to reach the reaction catalyst light off temperature, the combustion of the combustible fuel generating second combustion byproduct gases;

c. flowing a hydrogen-producing hydrocarbon fuel other than alcohol in the reaction zone to contact the reaction catalyst at the reaction catalyst light off temperature in a range of about 550 C. to about 650 C. to produce a reaction zone hydrogen gas mixture comprising hydrogen gas and reaction tail gases, wherein flowing the hydrocarbon fuel in the reaction zone further comprises:

c1. preheating water to at least about the boiling point of the hydrocarbon fuel to produce water vapor prior to contacting the water vapor with the hydrocarbon fuel;

c2. contacting the water vapor with the hydrocarbon fuel in the reaction zone whereby said contacting reduces carbon formation in the reaction chamber;

d. separating the hydrogen gas from the reaction zone hydrogen gas mixture through the hydrogen separation membrane, said hydrogen gas accumulated into the exhaust zone of the reactor chamber; and e. collecting the hydrogen gas from the exhaust zone of the reaction chamber.

2. The method of claim 1, wherein the hydrogen gas includes CO and/or $CO_2$, and collecting the hydrogen gas from the exhaust zone of the reaction chamber comprises:

e1. flowing the hydrogen gas through a methanator disposed in a reaction product line outside the reaction chamber and having a methanation catalyst to convert the CO and/or $CO_2$ to $CH_4$; and e2. storing at least part of the hydrogen gas.

3. The method of claim 1, wherein the flowing a hydrogen producing fuel in the reaction zone comprises:

c1a. contacting the hydrocarbon fuel with water vapor in a pre-reformer including a suitable catalyst to produce a pre-reformer hydrogen containing gas mixture; and c1b. flowing the resultant pre-reformer hydrogen containing gas mixture to the reaction zone.

4. The method of claim 3, further comprising:

f. condensing water vapor in the reaction tail gases by cooling followed by pressure reduction, obtaining condensed water and tail gases;

g. routing resultant tail gases to the combustion chamber; and h. recycling the condensed water.

5. The method of claim 1, wherein the combustion reaction is carried out in presence of water and the second combustion byproduct gases includes water vapor.

6. The method of claim 5, further comprising:
j. condensing water present in the combustion chamber byproduct gases by heat exchange with the incoming air to the combustion chamber;
k. recycling the water to the water supply; and
l. venting the cooled combustion chamber product gases to the atmosphere.

7. The method of claim 1, wherein hydrogen separation through the membrane can be improved by decreasing the hydrogen partial pressure in the hydrogen exhaust zone by employing a vacuum pump or a condensable inert gas.

8. A method for generating hydrogen in a hydrogen membrane reactor comprising:
providing in the reactor a catalytic combustion chamber defined by a bottom plate and a separation plate and communicating with a catalytic reaction chamber defined by a top plate and the separation plate, the reaction chamber having therein a planar hydrogen separation membrane defining a reaction zone and an exhaust zone, the catalytic combustion chamber comprising a plurality of combustion channels defined by a first set of spaced apart fins extending from the separation plate to and in contact with the bottom plate, the reaction zone comprising a plurality of reaction channels defined by a second set of spaced apart fins extending from the separation plate to and in contact with the planar hydrogen separation membrane, the reaction zone having a reaction catalyst therein, the method comprising:
injecting stored hydrogen into the combustion chamber at a first combustion light off temperature for a combustion catalyst in the combustion chamber;
injecting a second fuel different from the stored hydrogen concurrently with termination of stored hydrogen injection into the combustion chamber when temperature in the combustion chamber reaches a second combustion light off temperature for the combustion catalyst corresponding to the second fuel;
continuing injecting the second fuel into the combustion chamber to raise the temperature of the reaction catalyst to reach a third combustion light off temperature for the reaction catalyst;
injecting a hydrogen-producing hydrocarbon fuel other than alcohol into the reaction zone at or above the third combustion light off temperature in a range of about 550 C. to about 650 C. to produce a reaction zone hydrogen gas mixture comprising hydrogen gas and reaction tail gases, wherein injecting the hydrocarbon fuel into the reaction zone further comprises:
preheating water to at least about the boiling point of the hydrocarbon fuel to produce water vapor prior to contacting the water vapor with the hydrocarbon fuel;
contacting the water vapor with the hydrocarbon fuel in the reaction zone to reduce carbon formation in the reaction chamber; and
separating the hydrogen gas from the reaction zone gas mixture through the planar hydrogen separation membrane.

9. The method of claim 8, further comprising collecting and storing at least a part of the hydrogen gas from the exhaust zone of the reaction chamber.

10. The method of claim 9 further comprises passing the hydrogen gas through a methanator disposed in a reaction product line outside the reaction chamber and having a methanation catalyst to convert CO and/or $CO_2$ in the hydrogen gas to $CH_4$.

11. The method of claim 8, wherein injecting a hydrogen producing fuel into the reaction zone comprises:
contacting the hydrogen producing fuel with a reaction catalyst in a pre-reformer containing a suitable catalyst to produce a pre-reformer hydrogen containing gas mixture; and
passing the resultant pre-reformer hydrogen containing gas mixture to the reaction zone.

12. A method for generating hydrogen in a hydrogen membrane reactor comprising:
providing a planar catalytic combustion chamber defined between a bottom plate and a flat separation plate connected to and in thermal conduction communication with a planar catalytic reaction chamber defined between the separation plate and a top plate, the combustion chamber having therein a combustion catalyst, the planar reaction chamber having therein a planar hydrogen separation membrane defining a reaction zone and an exhaust zone, the planar catalytic combustion chamber comprising a plurality of combustion channels defined by a first set of spaced apart fins extending from the flat separation plate to and in contact with the bottom plate, the reaction zone comprising a plurality of reaction channels defined by a second set of spaced apart fins extending from the flat separation plate to and in contact with the planar hydrogen separation membrane, the reaction zone having a reaction catalyst therein, the method comprising:
injecting stored hydrogen into the combustion chamber at a combustion light off temperature for the combustion catalyst in the combustion chamber;
continuing injecting the stored hydrogen into the combustion chamber to raise the temperature of the reaction catalyst by conduction between the chambers to a combustion light off temperature for the reaction catalyst;
injecting a hydrogen-producing hydrocarbon fuel other than alcohol into the reaction zone at or above the combustion light off temperature for the reaction catalyst in a range of about 550 C. to about 650 C. to produce in the reaction zone a hydrogen gas mixture comprising hydrogen gas and reaction tail gases, wherein injecting the hydrocarbon fuel into the reaction zone further comprises:
preheating water to at least about the boiling point of the hydrocarbon fuel to produce water vapor prior to contacting the water vapor with the hydrocarbon fuel;
contacting the water vapor with the hydrocarbon fuel in the reaction zone to reduce carbon formation in the reaction chamber; and
separating the hydrogen gas from the reaction zone gas mixture through the hydrogen separation membrane.

13. The method of claim 12, further comprising collecting and storing at least a part of the hydrogen gas from the exhaust zone of the reaction chamber.

14. The method of claim 13 further comprises passing the hydrogen gas through a methanator disposed in a reaction product line outside the reaction chamber and having a methanation catalyst to convert CO and/or $CO_2$ in the hydrogen gas to $CH_4$.

15. The method of claim 12, wherein injecting a hydrogen producing fuel into the reaction zone comprises:

contacting the hydrogen producing fuel with a reaction catalyst in a pre-reformer containing a suitable catalyst to produce a pre-reformer hydrogen containing gas mixture; and passing the resultant pre-reformer hydrogen containing gas mixture to the reaction zone.

16. The method of claim 12, wherein the hydrogen producing fuel is the fuel injected into the combustion chamber.

17. The method of claim 1, wherein the combustion chamber contains a first catalyst coated substrate, the first catalyst coated substrate including pores and being in the form of a metal foam, monolith or mesh or a ceramic foam or monolith; and the reaction zone contains a second catalyst coated substrate, the second catalyst coated substrate including pores and being in the form of a metal foam, monolith or mesh or a ceramic foam or monolith.

18. The method of claim 8, wherein the catalytic combustion chamber contains a first catalyst coated substrate, the first catalyst coated substrate including pores and being in the form of a metal foam, monolith or mesh or a ceramic foam or monolith; and the reaction zone contains a second catalyst coated substrate, the second catalyst coated substrate including pores and being in the form of a metal foam, monolith or mesh or a ceramic foam or monolith.

19. The method of claim 12, wherein the planar catalytic combustion chamber contains a first catalyst coated substrate, the first catalyst coated substrate including pores and being in the form of a metal foam, monolith or mesh or a ceramic foam or monolith; and the reaction zone contains a second catalyst coated substrate, the second catalyst coated substrate including pores and being in the form of a metal foam, monolith or mesh or a ceramic foam or monolith.

* * * * *